US010928285B2

(12) United States Patent
Innes et al.

(10) Patent No.: US 10,928,285 B2
(45) Date of Patent: Feb. 23, 2021

(54) APPARATUS AND A METHOD FOR PERFORMING A STANDARD PENETRATION TEST

(71) Applicant: MARL TECHNOLOGIES INC., Edmonton (CA)

(72) Inventors: Murray Grant Innes, Edmonton (CA); Jerry Elford Wolverton, Edmonton (CA); Dustyn Jordan Lewis Elford, Sherwood Park (CA); Daniel Paul Teeuwsen, Sherwood Park (CA); Scott David Hughes, Sherwood Park (CA)

(73) Assignee: Marl Technologies Inc., Alberta (CA)

( * ) Notice: Subject to any disclaimer, the term of this patent is extended or adjusted under 35 U.S.C. 154(b) by 208 days.

(21) Appl. No.: 15/759,403

(22) PCT Filed: Sep. 15, 2016

(86) PCT No.: PCT/CA2016/051087
§ 371 (c)(1),
(2) Date: Mar. 12, 2018

(87) PCT Pub. No.: WO2017/045076
PCT Pub. Date: Mar. 23, 2017

(65) Prior Publication Data
US 2018/0259435 A1   Sep. 13, 2018

Related U.S. Application Data

(60) Provisional application No. 62/220,413, filed on Sep. 18, 2015.

(51) Int. Cl.
*G01N 33/24*   (2006.01)
*G01N 3/40*   (2006.01)
(Continued)

(52) U.S. Cl.
CPC ............... *G01N 3/40* (2013.01); *E02D 1/022* (2013.01); *G01N 33/24* (2013.01); *G01V 1/147* (2013.01)

(58) Field of Classification Search
None
See application file for complete search history.

(56) References Cited

U.S. PATENT DOCUMENTS 3,934,656 A * 1/1976 Pappert ............... E02D 1/022
173/124
3,998,090 A * 12/1976 Wislocki ............... B30B 11/027
73/12.12

(Continued)

FOREIGN PATENT DOCUMENTS

CA   2755534   4/2013
CA   2792568   4/2013
(Continued)

OTHER PUBLICATIONS

English Translation of CN-2064374-U (Year: 1990).*
(Continued)

*Primary Examiner* — Alexander A Mercado
(74) *Attorney, Agent, or Firm* — Kirsten M. Oates; Rodman & Rodman LLP

(57) ABSTRACT

A system for performing a standard penetration test, including a hammer assembly with a hammer and a hammer lifting device, an elevator assembly for raising and lowering the hammer assembly, a hammer sensor for sensing a position of the hammer within the hammer assembly, and an elevator sensor for sensing a position of the hammer assembly relative to the elevator assembly. A method for performing a standard penetration test, including positioning a hammer assembly at a hammer assembly ready position, sensing with an elevator sensor a reference position of a hammer assembly relative to the elevator assembly, sensing with a hammer (Continued)

sensor a zero position of a hammer, lifting the hammer with a hammer lifting device from the zero position to a drop position of the hammer, sensing with the hammer sensor the drop position, and dropping the hammer onto an anvil.

44 Claims, 9 Drawing Sheets

(51) Int. Cl.
*E02D 1/02* (2006.01)
*G01V 1/147* (2006.01)

(56) References Cited

U.S. PATENT DOCUMENTS

| | | | | | |
|---|---|---|---|---|---|
| 4,405,020 | A | * | 9/1983 | Rassieur | E21B 1/02 173/124 |
| 4,844,661 | A | * | 7/1989 | Martin | E02D 7/06 405/232 |
| 4,993,500 | A | * | 2/1991 | Greene | E02D 1/025 173/1 |
| 5,569,858 | A | * | 10/1996 | Askea | G01N 3/32 73/789 |
| 5,824,880 | A | * | 10/1998 | Burwell | G01N 3/303 73/12.06 |
| 6,301,551 | B1 | * | 10/2001 | Piscalko | E02D 13/06 340/853.8 |
| 6,575,253 | B2 | * | 6/2003 | Han | E02D 1/022 173/124 |
| 7,404,455 | B2 | | 7/2008 | Yue et al. | |
| 2003/0024713 | A1 | * | 2/2003 | Han | E02D 1/022 173/89 |
| 2004/0065453 | A1 | | 4/2004 | Tsai et al. | |
| 2007/0131025 | A1 | * | 6/2007 | Kinast | G01N 33/24 73/84 |
| 2007/0131453 | A1 | * | 6/2007 | Yue | E02D 1/022 175/20 |
| 2008/0307863 | A1 | * | 12/2008 | Sercel | G01N 3/303 73/84 |
| 2009/0283462 | A1 | * | 11/2009 | Schroeder | A47J 37/1223 210/106 |
| 2010/0030475 | A1 | | 2/2010 | Sohl, III et al. | |
| 2013/0103451 | A1 | | 4/2013 | Cockburn et al. | |
| 2014/0006074 | A1 | | 1/2014 | Cockburn et al. | |
| 2015/0007640 | A1 | * | 1/2015 | Gourves | G01N 3/32 73/85 |
| 2015/0114084 | A1 | * | 4/2015 | He | G01N 3/303 73/12.13 |
| 2016/0003724 | A1 | * | 1/2016 | Benz Navarrete | G01N 3/34 73/84 |
| 2016/0161362 | A1 | * | 6/2016 | Rastegar | G01N 3/307 73/12.07 |
| 2017/0131193 | A1 | * | 5/2017 | Yamamoto | G01V 8/20 |

FOREIGN PATENT DOCUMENTS

| | | | | |
|---|---|---|---|---|
| CN | 2064374 | U | * | 10/1990 |
| CN | 103911980 | | | 7/2014 |
| FR | 2938276 | | | 5/2010 |
| GB | 2314636 | A | * | 1/1998 ............... G01N 3/34 |
| JP | 10331142 | | | 12/1998 |
| JP | 2000110154 | | | 4/2000 |
| JP | 2001348858 | | | 12/2001 |
| KR | 20010044186 | | | 6/2001 |
| KR | 100419257 | | | 2/2004 |
| KR | 20040091317 | A | * | 10/2004 |
| KR | 100490661 | | | 5/2005 |
| KR | 100842186 | | | 7/2008 |
| KR | 100915544 | | | 9/2009 |
| KR | 20100091830 | | | 8/2010 |
| KR | 101256344 | | | 4/2013 |
| KR | 101478906 | | | 1/2015 |

OTHER PUBLICATIONS

English Translation of KR-20040091317-A (Year: 2004).*
Pile Dynamics, Inc., "Pile Dynamics, Inc. Company Profile", Sep. 1, 2015 (2 pages).
Wikipedia, the free encyclopedia, "Standard Penetration Test", https://en.wikipedia.org/wiki/Standard_penetration_test, Mar. 24, 2015 (3 pages).

* cited by examiner

APPARATUS AND A METHOD FOR PERFORMING A STANDARD PENETRATION TEST

TECHNICAL FIELD

An apparatus and a method for performing a standard penetration test (SPT).

BACKGROUND OF THE INVENTION

The standard penetration test (SPT) is a dynamic in situ test which is used to provide information regarding the properties of soil. The procedure for conducting a SPT is subject to engineering standards such as ASTM D1586 and ISO 22476-3.

In general terms, the SPT involves driving a sampler into the ground a standard test distance by dropping a hammer having a standard hammer weight from a standard drop height in order to advance the sampler. The number of blows of the hammer (i.e., the blow count) which are required to advance the sampler the standard test distance is recorded in three equal distance increments. The sum of the blow counts within the second and third distance increments is the "N" value.

According to ASTM D1586, the standard test distance is 18 inches, the standard hammer weight is 140 pounds ±2 pounds, the standard drop height is 30 inches ±1 inch, and each of the three distance increments is 6 inches.

According to ISO 22476-3, the standard test distance is 450 millimeters, the standard hammer weight is 63.5 kilograms ±0.5 kilograms, the standard drop height is 760 millimeters ±10 millimeters, and each of the three distance increments is 150 millimeters.

In performing a SPT test, the three distance increments are typically marked onto the sampler string with a grease marker so that the operator can observe when the sampler has advanced through each of the distance increments. The blow count within each of the three distance increments is counted and recorded by the operator.

The delivery of the hammer blows to the sampler is typically performed by raising and dropping a hammer onto an anvil which is positioned at a proximal end of a sampler string which includes the sampler at its distal end. As a result, the advancement of the sampler into the ground as a result of the hammer blows may be represented by the advancement of the anvil downward. The hammer blows may be delivered by raising and dropping the hammer manually, or with the assistance of an apparatus which automates to some extent the raising and dropping of the hammer.

One such apparatus is an "auto-hammer system" which automatically raises and drops a hammer onto an anvil positioned at a proximal end of a sampler string which includes a sampler at its distal end. In a typical auto-hammer system, a chain drive comprising a motor driving a vertically oriented chain cyclically raises the hammer above the anvil and releases the hammer in order to drop the hammer onto the anvil.

There are many potential sources of error in a typical SPT test, including:

1. the distance increments—since the operator is working along ground disturbed by a borehole, it may be difficult to ascertain the exact location of the ground surface. In addition, the grease markers which are typically used to mark the distance increments provide only a coarse indication, and the marking of the distance increments is often performed quickly at the possible expense of accuracy. These issues introduce potential errors in the starting and end points of the distance increments, the length of the distance increments, and the starting and end points of the SPT test;
2. the blow count—the counting of blows of the hammer is typically done mentally by the operator. Interruptions or distractions during the SPT test may introduce potential errors in the blow count, and the potential for error may increase as the blow count increases; and
3. the drop height—if the raising and dropping of the hammer is performed manually by the operator, potential errors may arise if the operator is not both careful and consistent in ensuring the standard drop height for each blow of the hammer. If the raising and dropping of the hammer is performed with the assistance of an automated apparatus such as the auto-hammer system, potential errors may arise if the height that the hammer is raised is not adjusted as the sampler is advanced during the SPT, and/or if the speed at which the hammer is lifted by the automated apparatus is not both controlled and consistent.

Errors in the performance of the SPT compromise the reliability and validity of the test results, and may result in over-design or under-design of projects which rely upon the test results.

SUMMARY OF THE INVENTION

References in this document to orientations, to operating parameters, to ranges, to lower limits of ranges, and to upper limits of ranges are not intended to provide strict boundaries for the scope of the invention, but should be construed to mean "approximately" or "about" or "substantially", within the scope of the teachings of this document, unless expressly stated otherwise.

The present invention is directed at a system and a method for performing a standard penetration test.

In an exemplary system aspect, the invention is a system for performing a standard penetration test comprising:
(a) a hammer assembly comprising a hammer and a hammer lifting device for lifting the hammer;
(b) an elevator assembly for raising and lowering the hammer assembly;
(c) a hammer sensor for sensing a position of the hammer within the hammer assembly; and
(d) an elevator sensor for sensing a position of the hammer assembly relative to the elevator assembly.

The system may be configured to operate using Imperial and/or Metric units. In some embodiments, the system may be configured to enable selection of Imperial and/or Metric units for the purpose of performing the standard penetration test and/or for the purpose of processing and/or presenting the test data.

The elevator assembly may comprise a mount for connecting the elevator assembly with the hammer assembly. The mount may comprise one or more suitable structures, devices or apparatus. The mount may be reciprocable vertically along the elevator assembly. The mount may be connected directly or indirectly with the hammer assembly.

The elevator assembly may comprise an elevator drive for reciprocating the mount vertically along the elevator assembly. The elevator drive may comprise one or more suitable structures, devices or apparatus. In some embodiments, the elevator drive may comprise an elevator cylinder and an elevator piston reciprocably contained within the elevator cylinder.

The elevator sensor may be associated with the elevator assembly. The elevator sensor may be associated with the elevator assembly in any suitable manner. In some embodiments, the elevator sensor may be associated with the elevator cylinder and the elevator piston so that sensing the position of the hammer assembly relative to the elevator assembly comprises sensing a position of the elevator piston relative to the elevator cylinder.

The elevator sensor may comprise one or more structures, devices or apparatus which are suitable for sensing the position of the hammer assembly relative to the elevator assembly. In some embodiments, the elevator sensor may comprise a linear displacement sensor.

In some embodiments, the elevator assembly may comprise an elevator velocity sensor for sensing an elevator velocity (i.e., a rate of change of the position of the hammer assembly relative to the elevator assembly). The elevator velocity sensor may comprise one or more structures, devices or apparatus which are suitable for sensing the elevator velocity. In some embodiments, the elevator velocity sensor may be comprised of the elevator sensor. In some embodiments, the elevator velocity sensor may be separate from the elevator sensor.

The elevator velocity sensor may sense an elevator velocity at any point, points, interval and/or intervals as the hammer assembly is being moved relative to the elevator assembly. In some embodiments, the elevator velocity sensor may sense the elevator velocity as the hammer assembly is being lowered relative to the elevator assembly.

The hammer lifting device may comprise one or more structures, devices or apparatus which are suitable for lifting the hammer.

In some embodiments, the hammer lifting device may engage with the hammer to lift the hammer and may disengage from the hammer to allow the hammer to drop.

In some embodiments, the hammer lifting device may comprise a chain drive. In some embodiments, the chain drive may comprise a lift link for engaging with the hammer in order to lift the hammer.

In some embodiments, the hammer assembly may comprise a hammer housing for containing the hammer.

The hammer sensor may be associated with the hammer assembly. The hammer sensor may be associated with the hammer assembly in any suitable manner. In some embodiments, the hammer sensor may be associated with the hammer housing and the hammer so that sensing the position of the hammer within the hammer assembly comprises sensing a position of the hammer relative to the hammer housing.

The hammer sensor may comprise one or more structures, devices or apparatus which are suitable for sensing the position of the hammer within the hammer assembly. In some embodiments, the hammer sensor may comprise a linear displacement sensor.

In some embodiments, the hammer assembly may comprise a lift counter. In some embodiments, the lifting of the hammer may comprise a lift event, and the lift counter may count lift events.

The lift counter may comprise one or more suitable structures, devices or

In some embodiments, the lift counter may be comprised of the hammer sensor. In some embodiments, the lift counter may be separate from the hammer sensor. In some embodiments, the lift counter may comprise a proximity sensor. In some embodiments in which the hammer lifting device comprises a chain drive and a lift link, the lift counter may sense the lift link in order to count lift events.

The hammer assembly may be configured to drop the hammer onto an anvil. In some embodiments, the anvil may be provided as a component of the system for performing a standard penetration test. In some embodiments, the anvil may be separate from the system for performing a standard penetration test. In some embodiments, the hammer assembly may comprise an anvil position sensor for sensing a position of the anvil relative to the hammer assembly.

The anvil position sensor may comprise any suitable sensor or combination of sensors. In some embodiments, the anvil position sensor may be comprised of the hammer sensor. In some embodiments, the anvil position sensor may be separate from the hammer sensor. In some embodiments, the anvil position sensor may comprise one or more proximity sensors.

In some embodiments, the anvil position sensor may comprise a first proximity sensor for providing an indication of whether the anvil is positioned at a desired location relative to the hammer assembly.

In some embodiments, the anvil may define a recess. An anvil may be fabricated to include a recess, or an anvil may be modified to provide a recess. In some embodiments, the first proximity sensor may be configured so that the anvil is or may be considered to be positioned at the desired location relative to the hammer assembly when the first proximity sensor senses the recess.

In some embodiments, the anvil position may comprise a second proximity sensor for providing an indication of whether the anvil is received within the hammer assembly. In some embodiments, the second proximity sensor may be configured so that the anvil is or may be considered to be received within the hammer assembly when the second proximity sensor senses the anvil.

In some embodiments, the hammer assembly may comprise a hammer velocity sensor for sensing a hammer velocity (i.e., a velocity of the hammer within the hammer assembly). The hammer velocity sensor may comprise one or more structures, devices or apparatus which are suitable for sensing the hammer velocity. In some embodiments, the hammer velocity sensor may be comprised of the hammer sensor. In some embodiments, the hammer velocity sensor may be separate from the hammer sensor.

The hammer velocity sensor may sense a hammer velocity at any point, points, interval and/or intervals as the hammer is being lifted and/or dropped. In some embodiments, the hammer velocity sensor may sense an anvil contact velocity (i.e., a hammer velocity as the hammer contacts the anvil). In some embodiments, the hammer velocity sensor may sense a maximum hammer velocity as the hammer is being lifted and/or dropped. In some embodiments, the hammer velocity sensor may sense an average hammer velocity as the hammer is being lifted and/or dropped.

In some embodiments, the hammer assembly may comprise an energy sensor for sensing an anvil contact energy which is delivered from the hammer to the anvil as the hammer contacts the anvil. The energy sensor may comprise one or more structures, devices or apparatus which are suitable for sensing the anvil contact energy. In some embodiments, the energy sensor may be comprised of the hammer sensor. In some embodiments, the energy sensor may be separate from the hammer sensor.

In some embodiments, the system may use software, algorithms and/or control loops instead of mechanical stops to provide range limiting or stop functions to the system. As a non-limiting example, the spool stroke of a valve or valves associated with a hydraulic system of the system may be controlled to obtain desired flow rates and pressures from the hydraulic system either mechanically or using software, an algorithm and/or a control loop. Mechanical control may require different setups for different hydraulic system and valve configurations, while software, algorithmic or control loop controls may potentially be more adaptable to different hydraulic system and valve configurations.

In some embodiments, the system may comprise a storage medium for storing data related to the standard penetration test. The storage medium may comprise one or more suitable structures, devices or apparatus.

In some embodiments, the system may comprise a computer network connected with the storage medium, for enabling remote access to the stored data. The computer network may comprise one or more suitable structures, devices or apparatus.

In an exemplary method aspect, the invention is a method for performing a standard penetration test comprising:
(a) providing:
 (i) a hammer assembly comprising a hammer and a hammer lifting device for lifting the hammer;
 (ii) an elevator assembly for raising and lowering the hammer assembly;
 (iii) a hammer sensor for sensing a position of the hammer within the hammer assembly; and
 (iv) an elevator sensor for sensing a position of the hammer assembly relative to the elevator assembly;
(b) positioning the hammer assembly at a hammer assembly ready position wherein an anvil is positioned at a desired location relative to the hammer assembly and wherein the hammer is resting upon the anvil;
(c) sensing with the elevator sensor a reference position of the hammer assembly relative to the elevator assembly when the hammer assembly is positioned at the hammer assembly ready position;
(d) sensing with the hammer sensor a zero position of the hammer within the hammer assembly when the hammer assembly is positioned at the hammer assembly ready position;
(e) lifting the hammer with the hammer lifting device from the zero position of the hammer to a drop position of the hammer;
(f) sensing with the hammer sensor the drop position of the hammer within the hammer assembly; and
(g) dropping the hammer onto the anvil from the drop position.

The method may be performed using either Imperial or Metric units.

In some embodiments, the method may comprise determining an actual drop height of the hammer. The actual drop height may be determined in any suitable manner. In some embodiments, the actual drop height may be determined from the drop position of the hammer and the zero position of the hammer.

In some embodiments, the method may comprise comparing the actual drop height of the hammer with a required drop height for the standard penetration test. In some embodiments, the method may comprise identifying the actual drop height as either compliant or non-compliant with the required drop height.

The hammer may be lifted in any suitable manner by the hammer lifting device. In some embodiments, lifting the hammer from the zero position of the hammer to the drop position of the hammer may comprise engaging the hammer lifting device with the hammer at the zero position, disengaging the hammer lifting device from the hammer at a maximum lifting height, and allowing inertia to lift the hammer from the maximum lifting height to the drop position.

The hammer may be lifted by the hammer lifting device at a hammer lifting speed. The hammer lifting speed may be constant or may be variable.

In some embodiments, lifting the hammer from the zero position of the hammer to the drop position of the hammer may comprise reducing the hammer lifting speed before the hammer reaches the maximum lifting height in order to reduce the inertia of the hammer.

The hammer lifting speed may be reduced in a single reduction or incrementally.

In some embodiments, the hammer lifting speed may be reduced incrementally between a ramp-down position of the hammer within the hammer assembly and the maximum lifting height.

In some embodiments, the method may comprise determining if the anvil is positioned at the desired location relative to the hammer assembly. Determining if the anvil is positioned at the desired location may be performed in any suitable manner.

The hammer may have a bottom position within the hammer assembly. The bottom position may be below the zero position. The bottom position of the hammer may be defined by a support on the hammer assembly which supports the hammer and prevents the hammer from moving within the hammer assembly below the bottom position. In some embodiments, determining if the anvil is positioned at the desired location relative to the hammer assembly may comprise sensing with the hammer sensor a position of the hammer relative to the bottom position.

In some embodiments, determining if the anvil is positioned at the desired location relative to the hammer assembly may comprise sensing with an anvil position sensor a position of the anvil relative to the hammer assembly. The anvil position sensor may comprise one or more suitable sensors. In some embodiments, the anvil position sensor may be comprised of the hammer sensor. In some embodiments, the anvil position sensor may be separate from the hammer sensor.

In some embodiments, the anvil position sensor may comprise one or more proximity sensors. In some embodiments, the anvil position sensor may comprise a first proximity sensor and a second proximity sensor.

The anvil may define a recess. An anvil may be fabricated to include a recess, or an anvil may be modified to provide a recess. In some embodiments, the recess may be used to determine if the anvil is positioned at the desired location relative to the hammer assembly. In some embodiments, the anvil position sensor may be configured so that the anvil is or may be considered to be positioned at the desired location relative to the hammer assembly when the anvil position sensor senses the recess and so that the anvil is not or is considered not to be positioned at the desired location relative to the hammer assembly when the anvil position sensor does not sense the recess. In some such embodiments, the anvil position sensor may comprise the first proximity sensor.

The anvil may have an upper end. In some embodiments, the anvil position sensor may be configured so that the anvil position sensor does not sense the anvil if the upper end of the anvil is below the anvil position sensor. In some embodiments, the anvil position sensor may be configured so that the anvil is or may be considered to be received within the hammer assembly when the anvil position sensor senses the anvil and so that the anvil is not or is considered not to be received within the hammer assembly when the anvil position sensor does not sense the anvil. In some such embodiments, the anvil position sensor may comprise the second proximity sensor.

In some embodiments, the method may comprise counting the lifting of the hammer as a lift event. Lift events may be counted in any suitable manner. In some embodiments, lift events may be counted using the hammer sensor. In some embodiments, lift events may be counted using a lift counter which is separate from the hammer sensor.

In some embodiments, counting the lifting of the hammer may comprise sensing a position of the hammer within the hammer assembly. In some such embodiments, the position of the hammer within the hammer assembly may be sensed with the hammer sensor. In some such embodiments, the position of the hammer within the hammer assembly may be sensed with a lift counter which is separate from the hammer sensor.

In some embodiments, counting the lifting of the hammer may comprise sensing a position of the hammer lifting device. In some embodiments, sensing a position of the hammer lifting device may comprise sensing a position of a component of the hammer lifting device, such as a lifting link in a chain drive. In some embodiments, the position of the hammer lifting device or of a component of the hammer lifting device may be sensed by a lift counter.

In some embodiments, the method may comprise sensing a hammer velocity at one or more points and/or intervals as the hammer is being lifted and/or dropped. The hammer velocity may be sensed in any suitable manner. In some embodiments, the hammer velocity may be sensed by the hammer sensor. In some embodiments, the hammer velocity may be sensed by a sensor which is separate from the hammer sensor.

In some embodiments, sensing a hammer velocity may comprise sensing an anvil contact velocity. In some embodiments, sensing a hammer velocity may comprise sensing a maximum hammer velocity. In some embodiments, sensing a hammer velocity may comprise sensing an average hammer velocity. In some embodiments, the hammer velocity may be used to determine the kinetic energy of the hammer.

In some embodiments, a hammer velocity when the hammer lifting device disengages from the hammer for a drop of the hammer and the zero position of the hammer for the drop of the hammer may be used as feedback for the purpose of achieving a compliant drop height of the hammer for a subsequent drop of the hammer. In some embodiments, the hammer velocity may be adjusted based upon a single previous drop of the hammer. In some embodiments, the hammer velocity may be adjusted based upon a plurality of previous drops of the hammer. In some embodiments, data relating to a number of previous drops of the hammer may be averaged in order to adjust the hammer velocity of the hammer for a subsequent drop of the hammer. In some embodiments, data relating to one or more drops of the hammer may be used in a proportional-integral-derivative (PID) loop to provide feedback for subsequent drops of the hammer.

After it is dropped, the hammer may deliver an anvil contact energy to the anvil. In some embodiments, the method may further comprise sensing the anvil contact energy. The anvil contact energy may be sensed in any suitable manner. In some embodiments, the anvil contact energy may be sensed by the hammer sensor. In some embodiments, the anvil contact energy may be sensed by a sensor which is separate from the hammer sensor. In some embodiments, the anvil contact energy may be sensed by a sensor which is attached to, connected to, or otherwise associated with the anvil.

In some embodiments, the method may comprise sensing an elevator velocity at one or more points and/or intervals as the hammer assembly is being moved relative to the elevator assembly. The elevator velocity may be sensed in any suitable manner. In some embodiments, the elevator velocity may be sensed by the elevator sensor. In some embodiments, the elevator velocity may be sensed by a sensor which is separate from the elevator sensor.

In some embodiments, sensing an elevator velocity may comprise sensing an elevator velocity as the hammer assembly is being lowered relative to the elevator assembly.

In some embodiments, an elevator velocity and/or a distance travelled by the hammer assembly when the hammer assembly is being lowered relative to the elevator assembly may be used as feedback for the purpose of increasing the efficiency of lowering the hammer assembly during a subsequent lowering of the hammer assembly. In some embodiments, the elevator velocity may be adjusted depending upon the distance that the hammer assembly is to be lowered relative to the elevator assembly. In some embodiments, the elevator velocity may be increased as the distance that the hammer assembly is to be lowered relative to the elevator assembly increases, and may be decreased as the distance that the hammer assembly is to be lowered relative to the elevator assembly decreases. In some embodiments, data relating to one or more sequences of lowering of the hammer assembly relative to the elevator assembly may be used in a proportional-integral-derivative (PID) loop to provide feedback for subsequent sequences of lowering the hammer assembly relative to the elevator assembly.

In some embodiments, the method may comprise:
(h) repositioning the hammer assembly at the hammer assembly ready position after dropping the hammer onto the anvil;
(i) sensing with the elevator sensor an updated reference position of the hammer assembly relative to the elevator assembly when the hammer assembly is repositioned at the hammer assembly ready position.
(j) sensing with the hammer sensor a zero position of the hammer within the hammer assembly when the hammer assembly is repositioned at the hammer assembly ready position;
(k) lifting the hammer with the hammer lifting device from the zero position of the hammer to the drop position of the hammer;
(l) sensing with the hammer sensor the drop position of the hammer within the hammer assembly;
(m) dropping the hammer onto the anvil from the drop position; and
(n) repeating (h) through (m) until the standard penetration test is complete.

In some embodiments, the method may comprise storing data related to the standard penetration test on a storage medium. Data may be stored in any suitable manner on any suitable storage medium.

In some embodiments, the method may comprise accessing the stored data from a remote location. The stored data may be accessed in any suitable manner using one or more suitable structures, devices or apparatus.

In some embodiments, the method may comprise:
(h) repositioning the hammer assembly at the hammer assembly ready position after dropping the hammer onto the anvil;

(i) sensing with the elevator sensor an updated reference position of the hammer assembly relative to the elevator assembly when the hammer assembly is repositioned at the hammer assembly ready position;
(j) sensing with the hammer sensor a zero position of the hammer within the hammer assembly when the hammer assembly is repositioned at the hammer assembly ready position;
(k) lifting the hammer with the hammer lifting device at a hammer lifting speed from the zero position of the hammer to the drop position of the hammer, wherein the hammer lifting speed is selected having regard to an actual drop height of a previous drop of the hammer;
(l) sensing with the hammer sensor the drop position of the hammer within the hammer assembly; and
(m) dropping the hammer onto the anvil from the drop position.

The hammer lifting speed may be selected to provide an actual drop height which is compliant with the required drop height for the standard penetration test. In some embodiments, the hammer lifting speed may be selected to be constant between the zero position of the hammer and the maximum lifting height. In some embodiments, the hammer lifting speed may be selected to be variable between the zero position of the hammer and the maximum lifting height. In some embodiments, the hammer lifting speed and/or a reduction in the hammer lifting speed between a ramp-down position of the hammer and the maximum lifting height may be selected to provide an actual drop height which is compliant with the required drop height for the standard penetration test.

In some embodiments, feedback may be provided to the system so that the hammer lifting speed and/or a reduction in the hammer lifting speed for a drop of the hammer may be adjusted based upon the actual drop height of one or more previous drops of the hammer.

In some embodiments, the hammer sensor may sense the advancement of the anvil downward as a result of a blow from the hammer. In some embodiments, the advancement of the anvil may be used to determine a velocity of the lifting device which will allow the hammer assembly to return to the ready position by the time the lifting device begins to lift the hammer for the next blow. In some embodiments in which the advancement of the anvil is relatively small, the velocity of the lifting device may be relatively fast. In some embodiments in which the advancement of the anvil is relatively large, the velocity of the lifting device may be relatively slow.

In some embodiments, the system may be configured so that the system cannot be paused once the lifting device has begun to lift the hammer. In such embodiments, if a pause command is issued to the system, the system may wait until the hammer has been fully lifted and dropped before the pause command is implemented. In some embodiments, the delay in implementing the pause command may be overridden by an emergency stop command.

In some embodiments, if the elevator assembly senses that the hammer assembly is considered to be at a bottom position relative to the elevator assembly and the hammer has travelled a sufficient distance during the test to complete the test, the test may be considered to be complete.

In some embodiments, if the elevator sensor senses that the hammer assembly is considered to be at a bottom position relative to the elevator assembly, the anvil sensor detects a missing anvil, and the hammer has not travelled a sufficient distance during the test to complete the test, the system may prevent the standard penetration test from continuing. In such embodiments, the operator may be provided with the options of aborting the test or considering the test to be complete based upon visual confirmation of the distance moved by the anvil or the sampler during the test.

In some embodiments, if the elevator sensor senses that the hammer assembly is considered to be at a bottom position relative to the elevator assembly, the anvil sensor does not detect a missing anvil, and the hammer has not travelled a sufficient distance during the test to complete the test, the operator may be provided with an option to add a rod extension to complete the test.

In some embodiments, the depth of the borehole in which the standard penetration test is being performed may be tracked, monitored and/or recorded. The depth of the borehole may be tracked, monitored and/or recorded in any suitable manner. In some embodiments, data relating to the depth of the borehole may be combined with test data relating to the standard penetration test so that the test data may be correlated with the depth data.

In some embodiments, an operator may be capable of overriding a determination of the depth of the borehole if the determination appears to be erroneous, or for any other reason.

In some embodiments, such overriding may be considered to be a bias. In some embodiments, such overriding may be retained for the duration of the drilling of the borehole.

In some embodiments, a determination of depth of the borehole may account for additional tools or structures which may be present in the borehole below the rod string which is performing the standard penetration test. A non-limiting example of such an additional tool or structure is a Shelby Tube Sampler. In some embodiments, the length of the additional tool or structure may be added to the depth determination either manually, semi-automatically, or automatically. As a non-limiting example, a button may be provided which when pushed, will automatically add a length (such as 18 inches) to the depth determination to account for the length of a standard Shelby Tube Sampler.

In some embodiments, one or more hammer blow rates as a function of time may be tracked, monitored and/or recorded. The hammer blow rates as a function of time may be tracked, monitored and/or recorded in any suitable manner. As a non-limiting example, the hammer blow rate as a function of time may be tracked, monitored and/or recorded by correlating the number of hammer blows which are counted by the lift counter with an elapsed time measurement provided by the system, or in some other manner. The hammer blow rate as a function of time may be expressed in any suitable unit, such as in hammer blows per minute. In some embodiments, the hammer blow rate as a function of time may be updated as the standard penetration test progresses.

In some embodiments, one or more hammer blow rates as a function of distance may be tracked, monitored and/or recorded. The hammer blow rates as a function of distance may be tracked, monitored and/or recorded in any suitable manner. As a non-limiting example, the hammer blow rate as a function of distance may be tracked, monitored and/or recorded by correlating the number of hammer blows which are counted by the lift counter with the distance travelled by the anvil as determined by the hammer sensor, or in some other manner. The hammer blow rate as a function of distance may be expressed in any suitable unit, such as in hammer blows per inch travelled by the anvil. In such embodiments, the system may provide for separate bins for storage of test data as a function of the distance travelled by the anvil. As a non-limiting example, if the hammer blow rate is expressed as hammer blows per inch, eighteen bins may be provided so that the hammer blow rate as a function of distance can be tracked, monitored and/or recorded for the duration of the standard penetration test.

In some embodiments, the average drop height of the hammer may be tracked, monitored and/or recorded. The average drop height of the hammer may be tracked, monitored and/or recorded in any suitable manner. In some embodiments, the average drop height may be tracked, monitored and/or recorded by averaging and/or processing data obtained by the hammer sensor relating to the drop heights for each of the hammer blows.

In some embodiments, the geographical location of a standard penetration test may be tracked, monitored and/or recorded. The geographical location may be tracked, monitored and/or recorded in any suitable manner. In some embodiments, geographical data relating to the location of the standard penetration test may be combined with test data so that the test data can be correlated with the geographical data. In some embodiments, the geographical data may be provided by a global positioning system (GPS) receiver.

In some embodiments, the method may be performed in a "soft soil start mode". The soft soil start mode may be used to allow a standard penetration test to begin without first ensuring that the hammer assembly is in the hammer assembly ready position. The soft soil start mode allows the system to track any sinking of the hammer which may be caused by the weight of the hammer on the anvil in soft soil. In such embodiments, if the operator determines that it is not possible to position the hammer assembly in the hammer assembly ready position without causing the anvil to sink in the soft soil, the operator may use the soft soil start mode to start the standard penetration test. In such embodiments, it is the operator's responsibility to ensure that the hammer is in contact with the anvil before starting the standard penetration test.

In some embodiments, if the anvil sinks in the soil under its own weight or under the weight of the hammer before the standard penetration test can be started, the operator may be provided with an option of inputting a measured or estimated distance that the anvil has sunk and then performing the standard penetration test for the remaining distance that the anvil must advance in order to complete the test.

In some embodiments, the method may be performed other than for the purpose of performing a standard penetration best. As one non-limiting example, the method may be used to perform other geotechnical tests such as a continuous cone penetration test, in which a cone is driven by a hammer and the hammer blows are recorded as a function of distance. As a second non-limiting example, the method may be used to perform calibrations and/or energy comparisons with outside systems.

BRIEF DESCRIPTION OF DRAWINGS

Embodiments of the invention will now be described with reference to the accompanying drawings, in which.

DETAILED DESCRIPTION

The present invention is directed at a system and a method for performing a standard penetration test.

Figure 1:
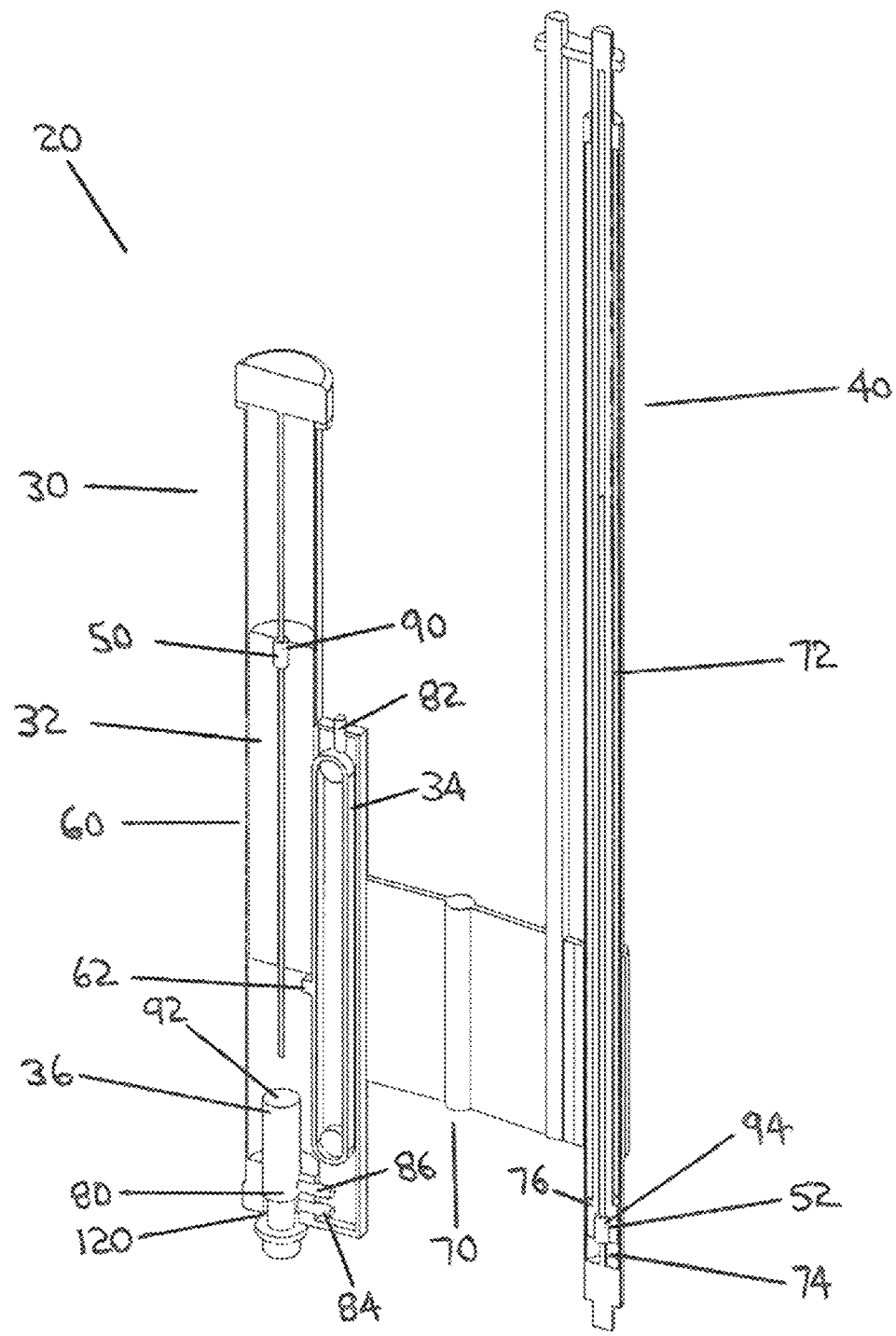
FIG. 1 is a schematic view of a first exemplary embodiment of a system for performing a standard penetration test.
Figure 2:
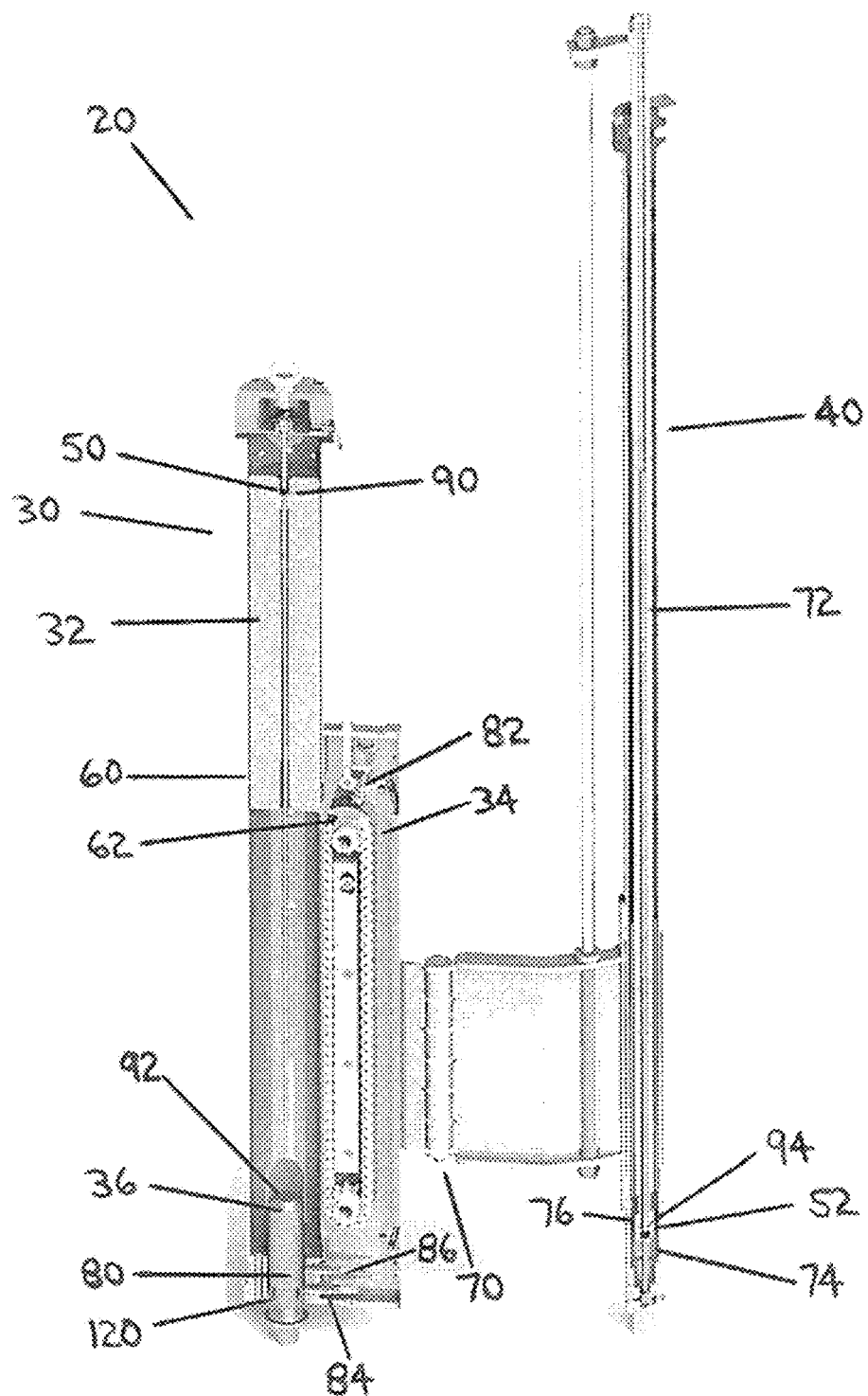
FIG. 2 is a longitudinal section assembly view of the system depicted in FIG. 1.
Figure 3:
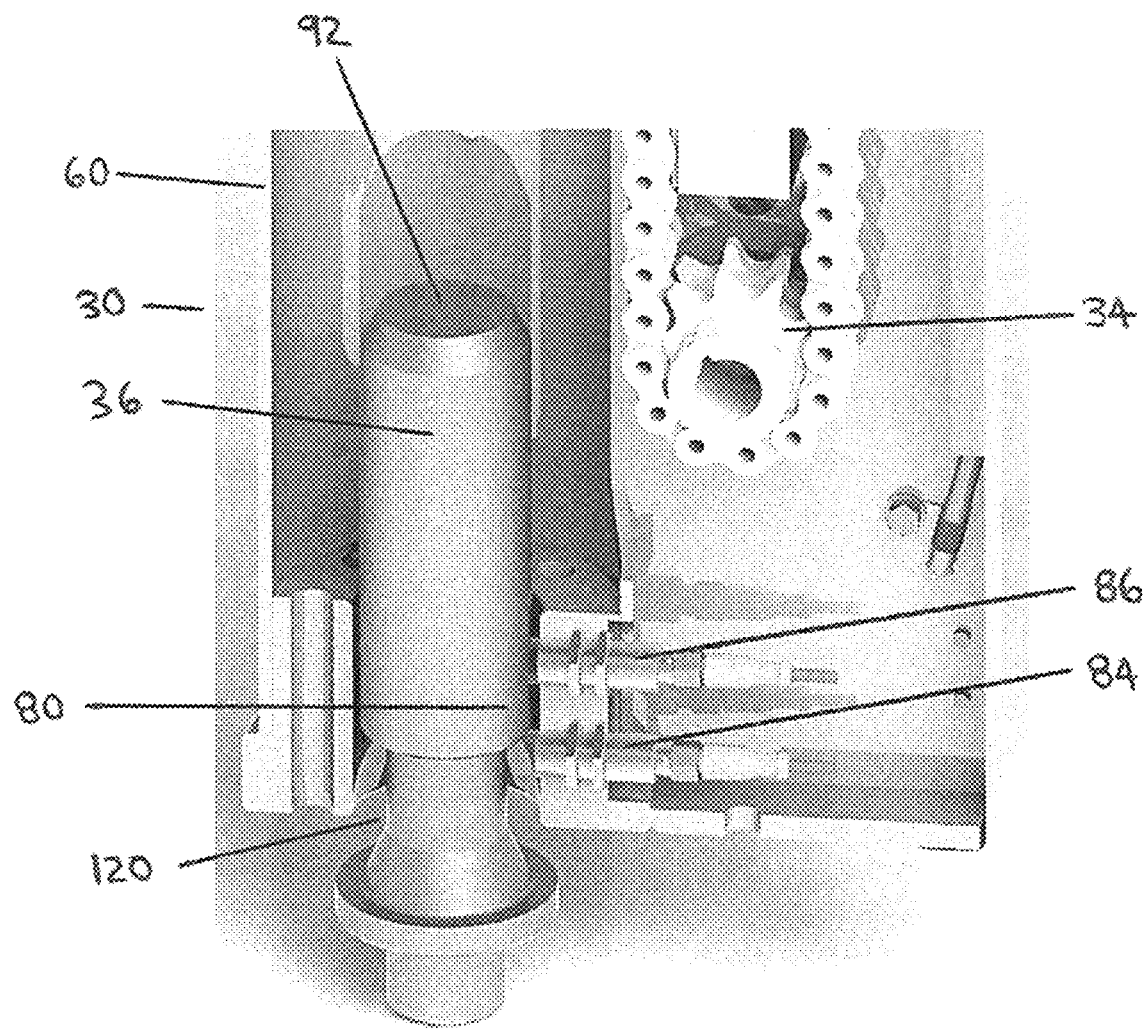
FIG. 3 is an isolated longitudinal section assembly view of an anvil, an anvil sensor, and an anvil missing sensor in the system depicted in FIG. 1.
Figure 4:
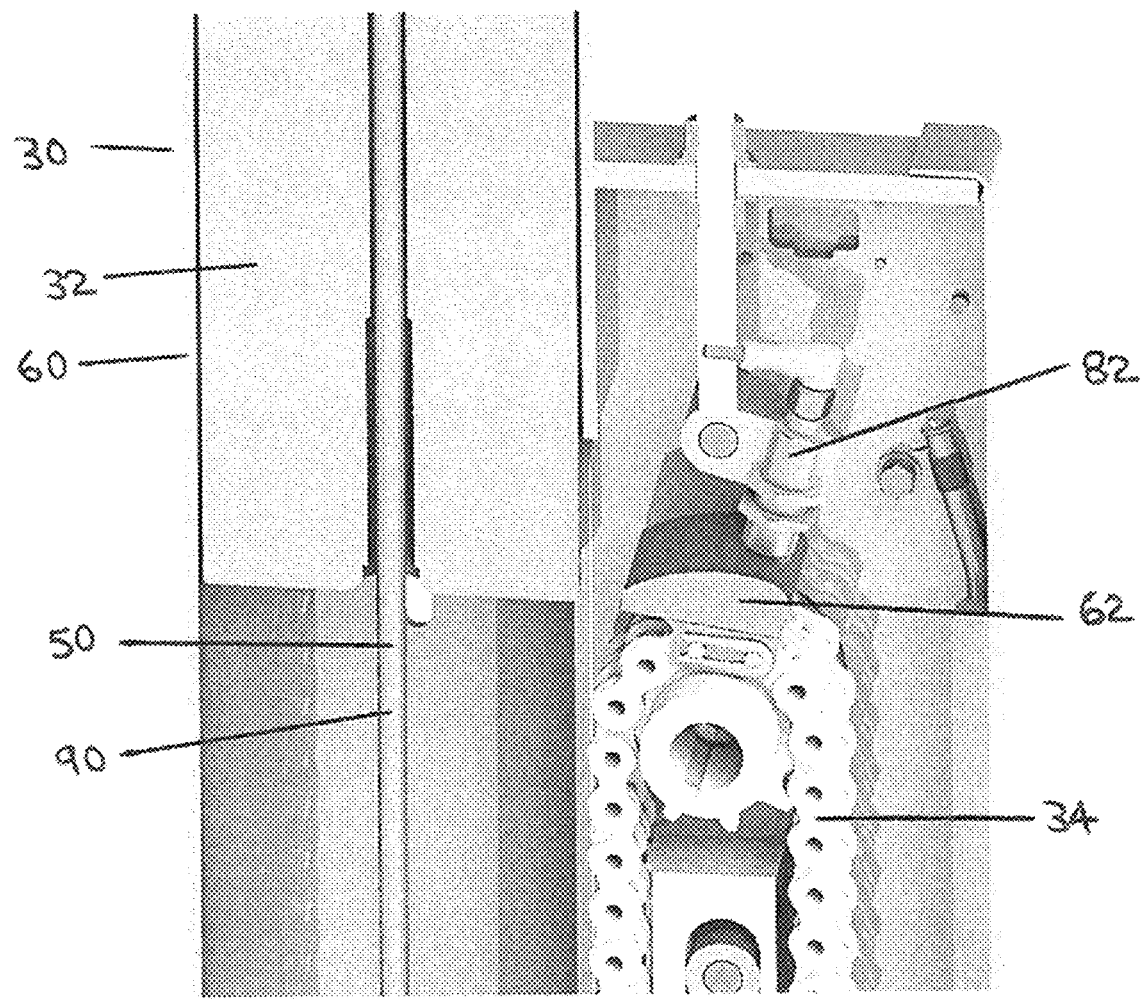
FIG. 4 is an isolated longitudinal section assembly view of a lift link sensor in the system depicted in FIG. 1.
Figure 5:
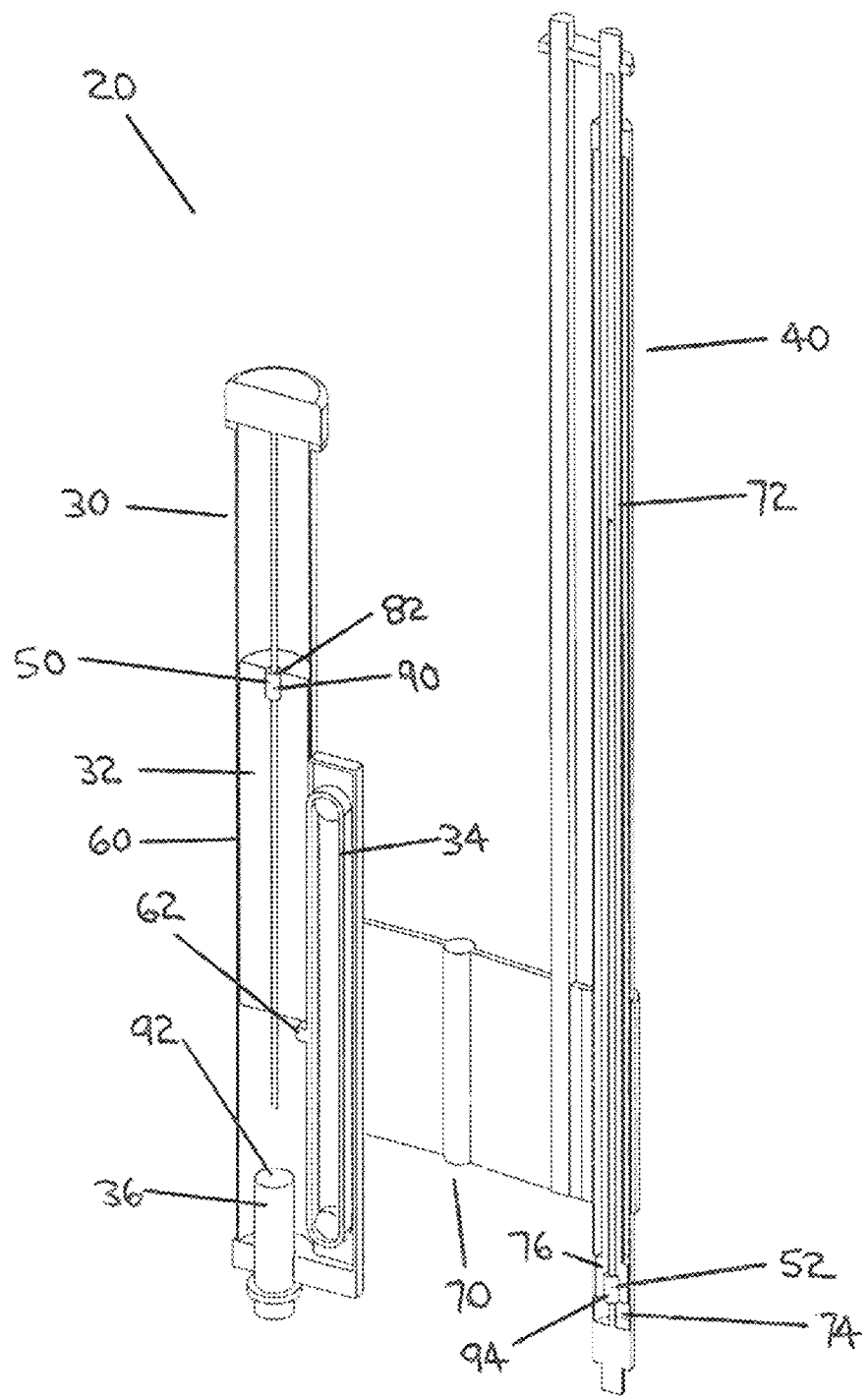
FIG. 5 is a schematic view of a second exemplary embodiment of a system for performing a standard penetration test.
Figure 6:
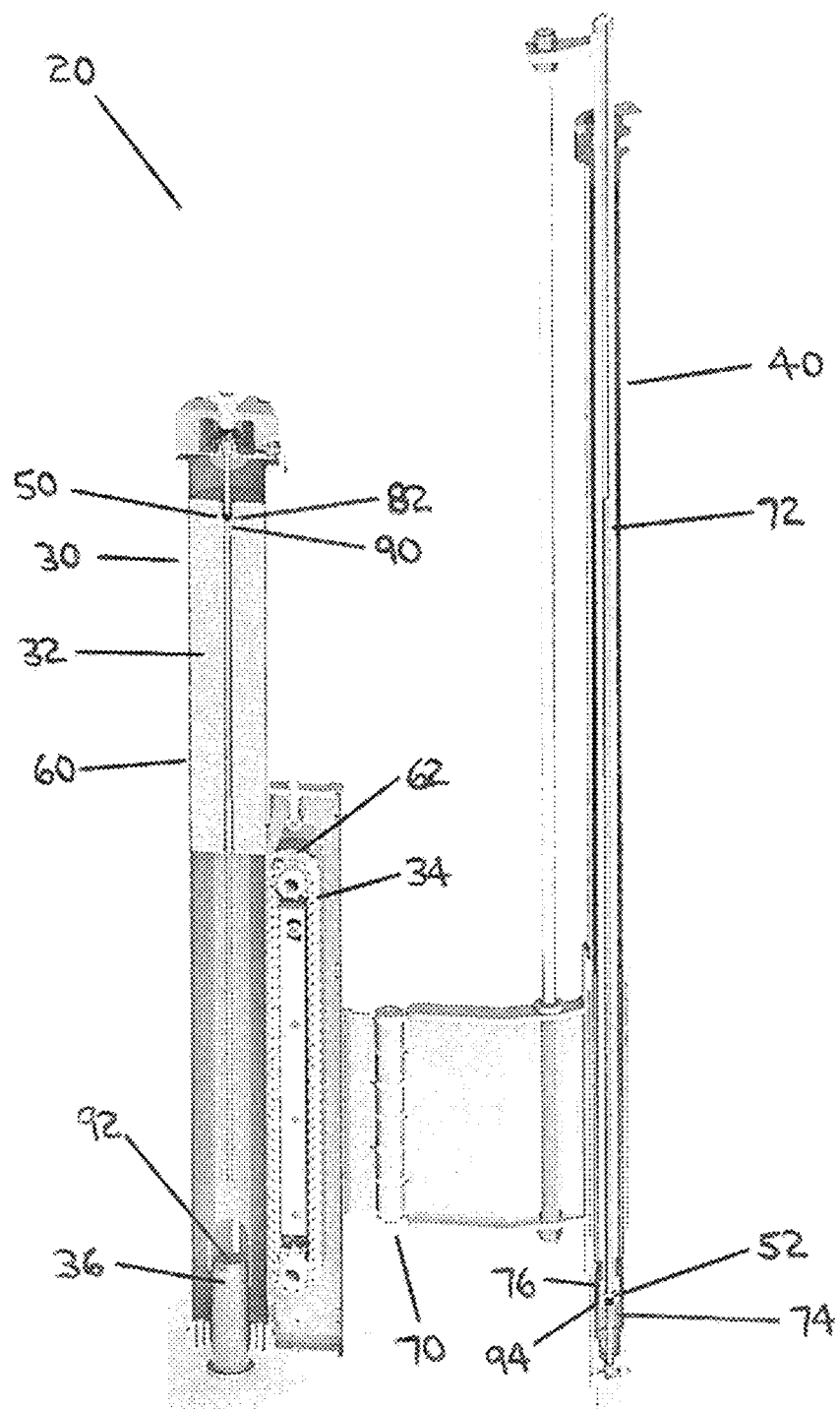
FIG. 6 is a longitudinal section assembly view of the system depicted in FIG. 5.
Figure 7:
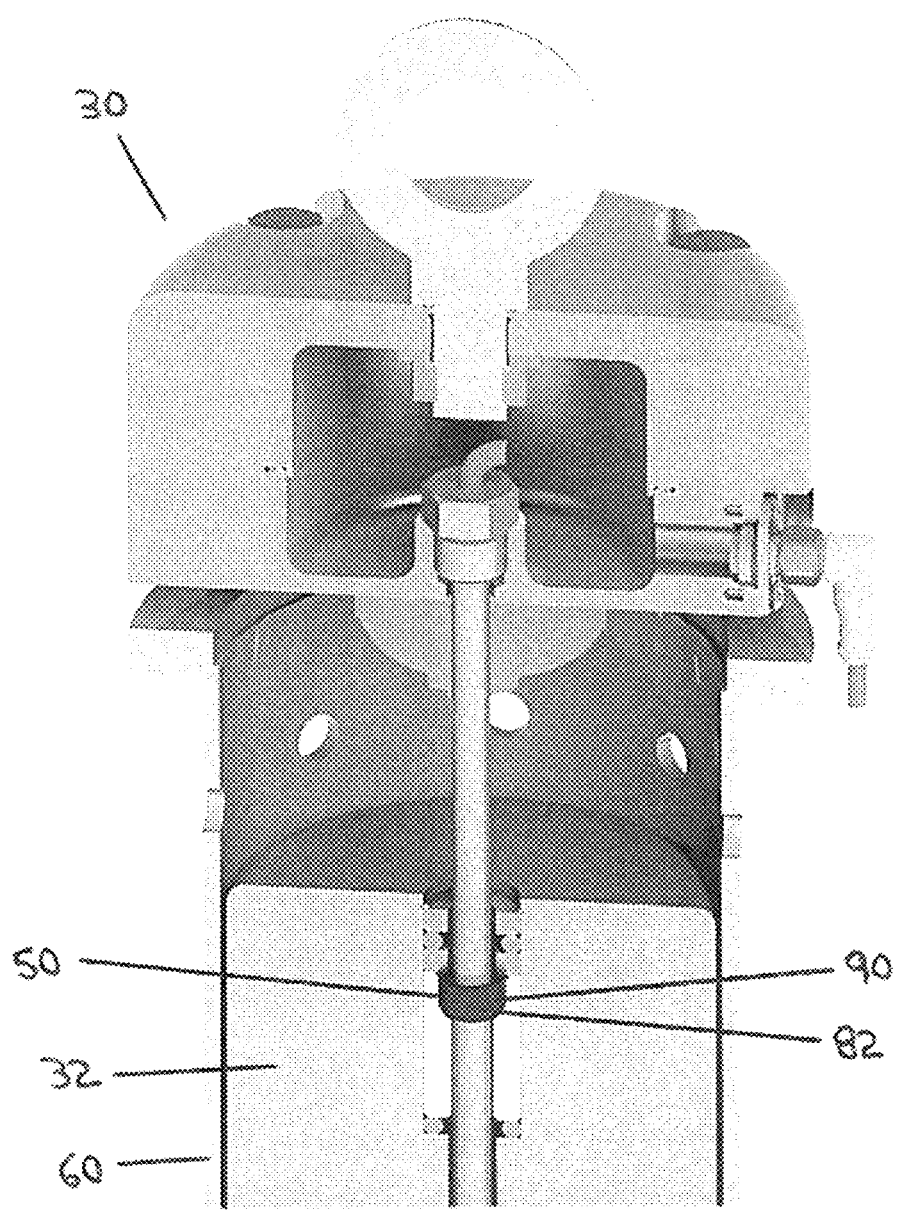
FIG. 7 is an isolated longitudinal section assembly view of features of a hammer sensor in the systems depicted in FIG. 1 and FIG. 5.
Figure 8:
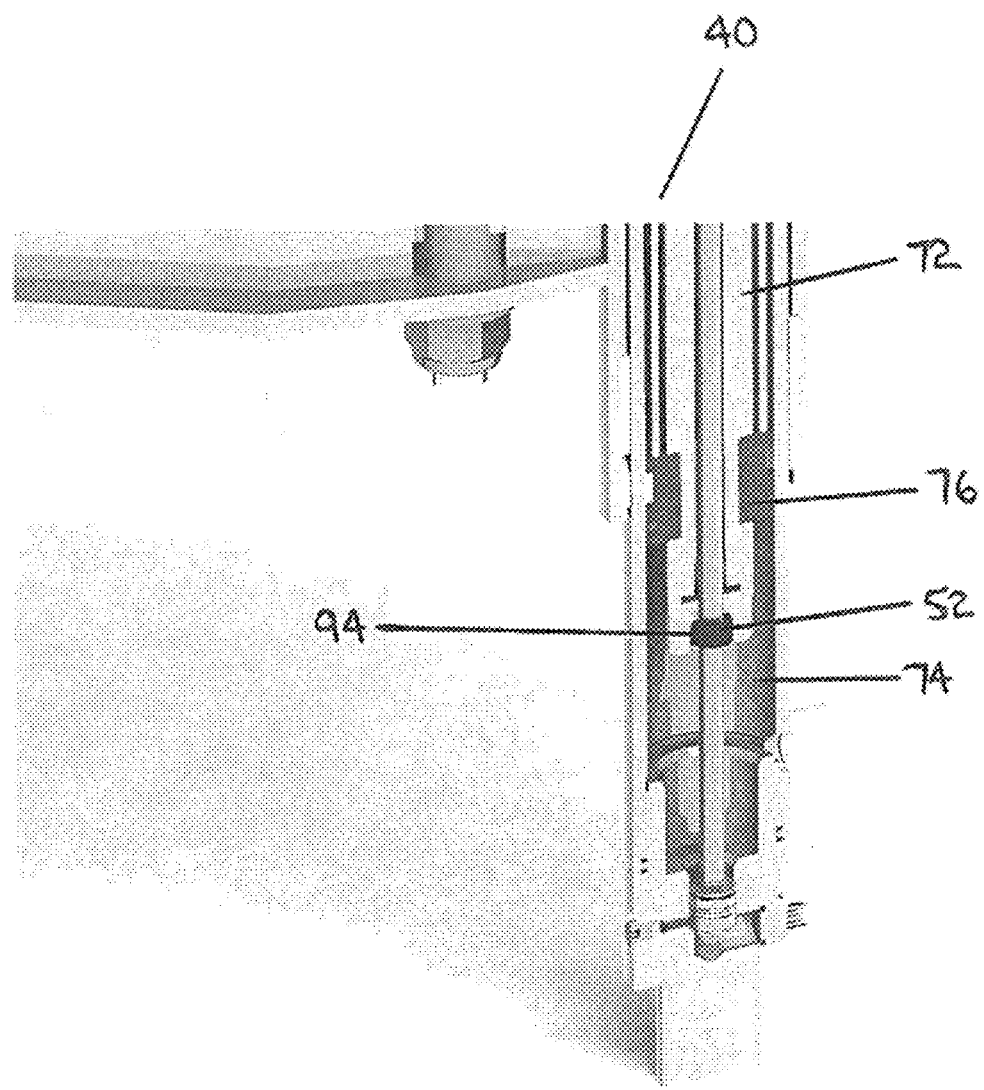
FIG. 8 is an isolated longitudinal section assembly view of features of an elevator sensor in the systems depicted in FIG. 1 and FIG. 5.
Figure 9:
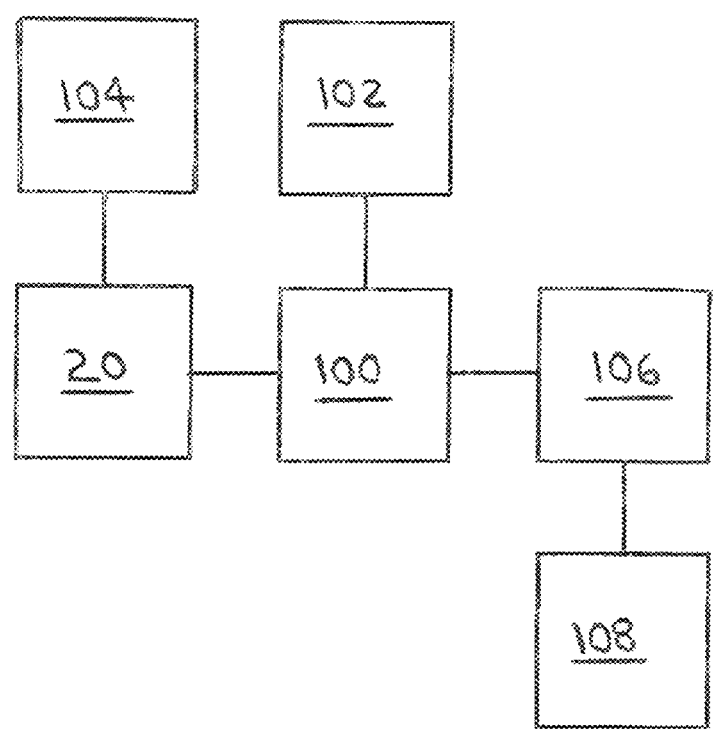
FIG. 9 is a schematic block diagram of an exemplary embodiment of a system comprising a storage medium for storing data related to a standard penetration test and a computer network associated with the storage medium for enabling remote access to the stored data.

FIGS. 1-4 depict a first exemplary embodiment of a system for performing a standard penetration test. FIGS. 5-6 depict a second exemplary embodiment of a system for performing a standard penetration test. FIG. 7 depicts features of a hammer sensor in the first exemplary embodiment and the second exemplary embodiment of the system for performing a standard penetration test. FIG. 8 depicts features of an elevator sensor in the first exemplary embodiment and the second exemplary embodiment of the system for performing a standard penetration test. FIG. 9 depicts an exemplary embodiment of a system comprising a storage medium for storing data related to a standard penetration test and a computer network associated with the storage medium for enabling remote access to the stored data.

FIGS. 1-9 and the descriptions of the exemplary embodiments are exemplary only. In the description of FIGS. 1-9 and the exemplary embodiments which follows, features which are identical or equivalent in FIGS. 1-9 and in the exemplary embodiments are identified with the same reference numbers.

Referring to FIGS. 1-9, in each of the exemplary embodiments, the system (20) comprises:
(a) a hammer assembly (30) comprising a hammer (32) and a hammer lifting device (34) for lifting the hammer (32);
(b) an elevator assembly (40) for raising and lowering the hammer assembly (30);
(c) a hammer sensor (50) for sensing a position and/or a velocity of the hammer (32) within the hammer assembly (30); and
(d) an elevator sensor (52) for sensing a position and/or a velocity of the hammer assembly (30) relative to the elevator assembly (40).

In the exemplary embodiments, the hammer assembly (30) comprises a hammer housing (60) for containing the hammer (32), and the hammer sensor (50) is associated with the hammer housing (60) and the hammer (32). In the exemplary embodiments, the hammer sensor (50) comprises a linear displacement sensor such as a linear displacement transducer (LDT), a linear variable differential transformer/transducer (LVDT), or similar sensor.

In the exemplary embodiments, the hammer lifting device (34) comprises a chain drive. The chain drive comprises a lift link (62) which engages with the hammer (32) to lift the hammer (32) and which disengages from the hammer (32) to allow the hammer (32) to drop onto an anvil (36). In the exemplary embodiments, the chain drive is driven by a chain drive motor (not shown), which in turn is driven by a hydraulic system (not shown) including a hydraulic pump (not shown).

In the exemplary embodiments, the elevator assembly (40) comprises a mount (70) and an elevator drive (72). The mount (70) is connected with the hammer assembly (30) and is reciprocable vertically along the elevator assembly (40) by the elevator drive (72). In both the first exemplary embodiment and the second exemplary embodiment, the elevator drive (72) comprises an elevator cylinder (74) and an elevator piston (76), and the elevator sensor (52) is associated with the elevator cylinder (74) and the elevator piston (76). In the exemplary embodiments, the elevator sensor (52) comprises a linear displacement sensor such as a linear displacement transducer (LDT) or a linear variable differential transformer/transducer (LVDT).

In the first exemplary embodiment, the hammer assembly (30) further comprises an anvil position sensor (80) and a lift counter (82). In the first exemplary embodiment, the anvil position sensor (80) comprises a first proximity sensor (84) for sensing whether the anvil (36) is positioned at a desired location relative to the hammer assembly (30) and a second proximity sensor (86) for sensing whether the anvil (36) is received within the hammer assembly (30). In the first exemplary embodiment, the lift counter (82) comprises a proximity sensor which senses the lift link (62) of the chain drive in order to count lift events.

In the second exemplary embodiment, the anvil position sensor (80) and the lift counter (82) are omitted. In the second exemplary embodiment, most or all of the functions of the anvil position sensor (80) and the lift counter (82) are performed using the hammer sensor (50).

In the exemplary embodiments, the system (20) may further comprise a hammer velocity sensor (90) for sensing a hammer velocity of the hammer (32) and/or an energy sensor (92) for sensing an anvil contact energy which is delivered from the hammer (32) to the anvil (36) as the hammer (32) contacts the anvil (36). In the exemplary embodiments, the hammer sensor (50) may function as the hammer velocity sensor (90).

In the exemplary embodiments, the system (20) may further comprise an elevator velocity sensor (94) for sensing an elevator velocity of the elevator assembly (40). In the exemplary embodiments, the elevator sensor (52) may function as the elevator velocity sensor (94).

Referring to FIG. 9, in the exemplary embodiments, the system (20) may further comprise a storage medium (100) for storing data recorded by the system (20), a processor (102) for processing data recorded by the system (20), a controller (104) for controlling the operation of the system (20), a computer network (106) for enabling access to data recorded by the system (20) from a remote location (108), and/or other equipment or apparatus (not shown) for enhancing the operation of the system (20).

The exemplary embodiments may be used on a vehicle, a skid or other structure (not shown) by mounting the elevator assembly (40) of the system (20) on the vehicle, skid or structure.

In the description of the exemplary embodiments which follows, the stated operating parameters are exemplary only and are based upon the current status of development of the system (20), and are subject to further development and/or optimization.

The First Exemplary Embodiment

The first exemplary embodiment of the system (20) for performing a standard penetration test includes 3 proximity sensors and 2 linear displacement sensors. The first exemplary embodiment of the system (20) may be used to perform a first exemplary embodiment of a method for performing a standard penetration test.

The first proximity sensor (84), referred to herein as the "anvil sensor", senses when the anvil (36) is in position. The second proximity sensor (86), referred to herein as the "anvil missing sensor", senses if the anvil (36) is received within the hammer assembly (30). A third proximity sensor senses each time the lift link (62) travels around the top sprocket of the chain drive and thus functions as the lift counter (82).

The hammer sensor (50), comprising a first linear displacement sensor, tracks the hammer (32) within the hammer assembly (30) and the elevator sensor (52), comprising a second linear displacement sensor, tracks the elevator piston (76) within the elevator cylinder (74).

All of the proximity sensors (84, 86, 82) are normally-closed sensors, which means that they are always "on" unless they detect something. This feature allows a defective sensor to be detected and to prevent a standard penetration test from being performed with a defective sensor.

An objective of the first exemplary embodiment of the system (20) is to meet strictly all of the parameters set out by the ASTM standard D1586-11.

Referring to FIGS. 1-4 and 7-9, the first exemplary embodiment of the system (20) may be operated as follows in order to provide a first exemplary embodiment of a method for performing a standard penetration test:

1. in preparation for a standard penetration test, the hammer (32) is at rest at its bottom position within the hammer housing (60);
2. the anvil (36) (having a recess (120)) is inserted within the hammer housing (60) with the hammer (32) resting on it until both the anvil sensor (84) and the anvil missing sensor (86) can sense the anvil (36). In the first exemplary embodiment, if the anvil sensor (84) (or in an alternate configuration, the anvil missing sensor (86)) cannot sense the anvil (36), the system (20) will prevent a test from being started or continued. This feature prevents an inadvertent start-up of the system (20) if the anvil (36) is not received within the hammer assembly (30);
3. in the first exemplary embodiment, if the anvil sensor (84) senses the anvil (36) (thereby indicating that the anvil (36) is received within the hammer assembly (30)), the operator may push a start button in order to lower the hammer assembly (30) with the elevator assembly (40) until the anvil sensor (84) senses the recess (120) in the anvil (36), indicating that the anvil (36) is at its desired location relative to the hammer assembly (30). At this point, a stop command is sent to the elevator assembly (40) and the position sensed by the elevator sensor (52) is recorded as an initial reference position of the hammer assembly (30) relative to the elevator assembly (40). With hydraulic systems, there is always a little bit of overflow. Because of this overflow, a time delay of 300 ms is added to allow the system (20) to settle and to allow an accurate hammer position to be recorded with the hammer sensor (50). This hammer position is the zero position of the hammer (32);
4. the chain drive motor is commanded to start rotating the chain drive, which causes the lift link (62) to engage and lift the hammer (32). In the first exemplary embodiment, the chain drive motor is initially driven at 70 percent of its maximum speed to provide an initial hammer lifting speed. The position of the hammer (32)

within the hammer assembly (30) is tracked by the hammer sensor (50) as the hammer (32) is lifted. In the first exemplary embodiment, when the hammer (32) is lifted to 24.4 inches above the zero position, the speed of the chain drive motor and the hammer lifting speed begin to reduce;

5. in the first exemplary embodiment, the position of the hammer (32) within the hammer assembly (30) controls the ramp-down of the hammer lifting speed at a rate of 20% per inch to a minimum chain drive speed of 20 percent of the maximum speed of the chain drive motor. It is important that the valve of the hydraulic system which drives the chain drive motor produces a consistent flow for the ramp-down of the hammer lifting speed to be reliable. Because of the reliance on hydraulic flow, in the first exemplary embodiment the RPM of the rig engine (not shown) is automatically set to a minimum of 50% of the maximum allowed RPM when the standard penetration test begins. In other embodiments, other steps may be taken to ensure that an adequate and consistent flow of hydraulic fluid is provided to components of the system (20) such as the chain drive motor;

6. in the first exemplary embodiment, the ramp-down of the hammer lifting speed reduces the inertia of the hammer (32) so that when the lift link (62) disengages from the hammer (32) at the maximum lifting height, the hammer is "tossed" upward about 0.75 inch to the drop position of the hammer (32). As the lift link (62) passes over the top sprocket of the chain drive, the lift counter (82) senses the lift link (62) and counts the occurrence as a lift event. The hammer sensor (50) senses the drop position before the hammer (32) drops. The difference between the drop position and the zero position represents the actual drop height and is recorded as the actual drop height for the drop of the hammer (32) upon the anvil (36). The actual drop height is compared with the ASTM standard (D1586-11) range of 29-31 inches. If the actual drop height falls within the standard range the drop is recorded as a passed drop. If the actual drop height falls outside the standard range the drop is recorded as a failed drop;

7. in the first exemplary embodiment, after the drop of the hammer (32) is sensed by the hammer sensor (50), the final reduced ramp-down speed of the chain drive motor is continued for 600 ms which provides time for the hammer (32) to impact the anvil (36), for the anvil sensor (84) to sense whether the anvil (36) remains in its desired location relative to the hammer assembly (30) and if necessary, for the elevator assembly (40) to reposition the hammer assembly (30) at the hammer assembly ready position. If the hammer assembly ready position has not been established by the end of the 600 ms, the chain drive motor is commanded to stop. If the hammer assembly ready position has been established by the end of the 600 ms, the chain drive motor resumes travel at full speed (i.e., at 70 percent of its maximum speed);

8. in the first exemplary embodiment, when the hammer (32) impacts the anvil (36), the anvil (36) is advanced downward. If the anvil (36) advances downward enough to trip the anvil sensor (84), a command is sent to the elevator assembly (40) to reposition the hammer assembly (30) at the hammer assembly ready position. The hammer assembly (30) continues to be lowered by the elevator assembly (40) until the anvil sensor (84) senses that the anvil (36) has been returned to its desired location relative to the hammer assembly (30), and then stops. The time delay of 300 ms is provided again to account for hydraulic overflow. The position of the hammer (32) within the hammer assembly (30) is sensed by the hammer sensor (50) and recorded as the new zero position of the hammer (32). The position of the hammer assembly (30) relative to the elevator assembly (40) is sensed by the elevator sensor (52) and is recorded as an updated reference position of the hammer assembly (30) relative to the elevator assembly (40);

9. in the first exemplary embodiment, the above described procedure is repeated until the elevator sensor (52) senses that the hammer assembly (32) has been lowered 18 inches relative to the initial reference position. The blows of the hammer (32) upon the anvil (36) are recorded in distance increments of 6 inches, so while the position of the hammer assembly (30) relative to the elevator assembly (40) is between 0-5.9 inches from the initial reference position the blows are counted towards a "first count", while the position of the hammer assembly (30) relative to the elevator assembly (40) is between 6-11.9 inches from the initial reference position the blows are counted towards a "second count", and while the position of the hammer assembly (30) relative to the elevator assembly (40) is between 12-17.9 inches from the initial reference position the blows are counted towards a "third count"; and 10. when the position of the hammer assembly (30) relative to the elevator assembly (40) has moved 18 inches from the initial reference position, the standard penetration test is stopped. Referring to FIG. 9, in the first exemplary embodiment the recorded data may be stored on a suitable storage medium (100) such as a disk and/or a server, and if desired may be made available via a computer network (106) to be accessed from a remote location (108).

The first exemplary embodiment of the system (20) and method may include additional features.

Bottom Stroke Detection Zone

Since the position of the hammer assembly (30) relative to the elevator assembly (40) is sensed by the elevator sensor (52), the system (20) can be configured to provide an indication when the elevator assembly (40) reaches the bottom of its stroke. If for some reason a standard penetration test is started without enough travel in the elevator assembly (40) to successfully complete the test, the test will need to be paused when the elevator assembly (40) reaches the bottom of its stroke. A rod extension (not shown) may then be added to the sampler string under the anvil (36), and the test may be continued from where it was paused. In the first exemplary embodiment, a bottom stroke detection zone is currently set at 0.5 inches from the end of travel of the elevator assembly (40) (the length of the bottom stroke detection zone may be subject to further optimization).

When the bottom stroke detection zone is encountered during a standard penetration test and the test is paused, the total distance travelled by the hammer assembly (30) from the initial reference position is recorded, and only the controls to the elevator assembly (40) are enabled. This allows the operator to move the hammer assembly (30) off the anvil (36), remove the anvil (36) from the sampler string (not shown), add a rod extension to the sampler string, and reattach the anvil (36) to the sampler string. After the anvil (36) is reattached to the sampler string, the operator is able to reposition the hammer assembly (30) at the hammer assembly ready position as if beginning a new test. The operator may push a resume button in order to command the system to reposition the hammer assembly (30) at the hammer assembly ready position. When the anvil sensor (84) senses that the anvil (36) is at its desired location relative to the hammer assembly (30), the position of the hammer assembly (30) relative to the elevator assembly (40) is recorded by the elevator sensor (52) as an updated reference position. As the standard penetration test resumes the distance travelled by the hammer assembly (30) relative to the elevator assembly (40) before the test was paused is added to the distance travelled by the hammer assembly (30) from the updated reference position. This feature enables the operator to continue the test without losing any information.

Prior to allowing the start of a standard penetration test, the system (20) will provide a warning if the elevator assembly (40) does not have sufficient travel to complete the test. In such circumstances, the operator has the ability to start the test after the warning is provided, but will be made aware by the warning that it will be necessary to interrupt the test to add a rod extension before the test can be completed.

Anvil Position Sensor (80)

The anvil position sensor (80) may comprise one or more sensors. In the first exemplary embodiment, the anvil position sensor (80) comprises the anvil sensor (84) and the anvil missing sensor (86).

The anvil sensor (84) is used to determine when the anvil (36) is positioned at its desired location relative to the hammer assembly (36), by sensing the recess (120) in the anvil (36) (i.e., by sensing an absence of anvil material). This is potentially problematic because a missing anvil (36) may also result in the anvil sensor sensing an absence of anvil material.

This issue is addressed in the first exemplary embodiment by the anvil missing sensor (86), which is positioned above the anvil sensor (84) and which indicates a missing anvil event if it fails to sense anvil material. If the anvil missing sensor (86) and the anvil sensor (84) both sense a lack of anvil material, the anvil (36) is assumed to be missing (i.e., not received within the hammer assembly (30)).

In the first exemplary embodiment, when the anvil (36) is determined to be missing during a test, the test pauses as it does when the bottom stroke detection zone is encountered, but the system (20) continues to track the total test distance as the operator attempts to reposition the hammer assembly (30) at the hammer assembly ready position in order to continue the test. If the total test distance reaches 18 inches as the operator attempts to reposition the hammer assembly (30) at the hammer assembly ready position, the test is considered to be complete.

Right of Refusal Conditions

The ASTM standard (D1586-11) defines a standard penetration test to be complete if any one of five conditions occur. One condition occurs if the anvil (36) advances 18 inches during a test, which means that the test has been successfully completed. A second condition occurs if the anvil (36) sinks in soft soil under the weight of the sampler string and the hammer (32).

The other three conditions are referred to as "right of refusal" conditions:
1. if 50 blows of the hammer (32) are reached within any 6 inch distance increment in a test;
2. if 100 total blows of the hammer (32) are reached in a test; and
3. if 10 consecutive blows at any point during a test do not advance the anvil (36).

In the first exemplary embodiment, the system (20) is configured to track right of refusal conditions and to pause a test if any right of refusal condition occurs. The system (20) indicates the occurrence of a right of refusal condition to the operator (visually and/or audibly or in any other suitable manner) and requires the operator to provide a command to the system (20) either to end the test or to continue the test (in some circumstances, valuable information may be obtained if the test is allowed to continue following the occurrence of a right of refusal condition).

In the first exemplary embodiment, the system (20) records the command which is provided by the operator following the occurrence of a right of refusal condition.

In the first exemplary embodiment, the distance threshold for the third right of refusal condition is 0.1 inch. In other words, in the first exemplary embodiment, the third right of refusal condition is considered to occur if the anvil (36) does not advance at least 0.1 inch as a result of 10 consecutive blows. This distance threshold is currently based in part upon the resolution of the elevator sensor (52). This distance threshold may be subject to further refinement and/or optimization.

Soft Soil Detection

As mentioned above, one of the five conditions under which the ASTM standard (D1586-11) considers a test to be complete occurs if the anvil (36) sinks in soft soil under the weight of the sampler string and the hammer (32).

To capture this occurrence, the system (20) compares the change in the position of the hammer (32) within the hammer assembly (30) (as sensed by the hammer sensor (50)) with the change in the position of the hammer assembly (30) relative to the elevator assembly (40) (as sensed by the elevator sensor (52)) while the elevator assembly (40) is lowering the hammer assembly (30) in order to position or reposition the hammer assembly (30) at the hammer assembly ready position.

If the hammer (32) is not moving upward within the hammer assembly (30) at the same rate as the hammer assembly (30) is moving downward relative to the elevator assembly (40), the anvil (36) may be sinking downward. The ASTM standard provides that if an anvil (36) sinks, the distance it sinks is to be recorded to the nearest 0.1 foot, the test is to be completed to 18 inches (whether by continuing to lower the hammer assembly (30) or by using more blows of the hammer (32)), and the weight of the sampler string and the hammer (32) is to be recorded as the N-value. Because the ASTM standard requires the distance to be recorded to the nearest 0.1 foot, 0.1 foot is used in the system (20) as the threshold distance for determining if the anvil (36) is sinking.

A known issue with soft soil is that if the hammer assembly ready position is not achieved before the lift link (62) engages the hammer (32), the lift link (62) can push against the side of the hammer (32). This pushing of the hammer (32) by the lift link (62) may cause the hammer (32) to bind inside the hammer housing (60), with the result that the command to the elevator assembly (40) to lower the hammer assembly (30) may cause the elevator assembly (40) to push the anvil (36) downward.

This issue is addressed in the system (20) in part by the 600 ms time delay after a drop of the hammer (32) is sensed by the hammer sensor (50). If the hammer assembly (30) is not repositioned to the hammer assembly ready position by the end of the time delay, the chain drive motor is commanded to stop so that the lift link does not run into the side of the hammer (32).

Also, when a test is started, there is no way of knowing exactly where the lift link (62) is positioned along the chain drive, so a further time delay of 100 ms in addition to the 300 ms time delay which is provided to allow for hydraulic overflow (i.e., a total time delay of 400 ms) is used during repositioning of the hammer assembly (30) to ensure that the hammer assembly (30) is at the hammer assembly ready position before the lift link (62) engages the hammer (32).

One Repositioning of the Hammer Assembly (30) Per Hammer Blow

The elevator assembly (40) could be commanded to reposition the hammer assembly (30) if the anvil (36) advances due to the working vibrations of the system (20) while the hammer (32) is already being lifted for another drop.

Because of the 0.1 inch resolution of the elevator sensor (52), it is possible to have an anvil (36) advancement of 17.9 inch which would require at least one more blow of the hammer (32) in order to complete the test to 18 inches.

As a result, in some circumstances a small advancement of the anvil (36) due to system (20) vibrations or other causes could result in the test being completed by the anvil (36) moving past 18 inches while the hammer (32) is already being lifted to deliver a blow to the anvil (36), resulting in the hammer (32) falling from an unknown height (caused by the movement of the hammer assembly (30) by the elevator assembly (40) while the hammer (32) is being lifted) and a potentially unreliable blow by the hammer (32) to the anvil (36).

This issue is addressed in the first exemplary embodiment of the system (20) by restricting the actuation of the elevator assembly (40) during the final 0.5 inch of advancement of the anvil (36) so that only one repositioning of the hammer assembly (30) is allowed per drop of the hammer (32). As a result, in the first exemplary embodiment, if the anvil (36) has advanced 17.9 inches and the hammer assembly (30) has been repositioned to the hammer assembly ready position, the elevator assembly (40) will not be able to reposition the hammer assembly (30) again until after the hammer (32) has been lifted and dropped.

Aborted Tests

The ASTM standard (D1586-11) requires that if a standard penetration test is not completed to 18 inches of advancement of the anvil (36), the amount of advancement of the anvil (36) when a test is aborted is to be recorded. The system (20) records both the occurrence of an aborted test and the amount of advancement of the anvil (36) when the test is aborted.

Amount of Advancement of the Anvil Per Blow of the Hammer

The distance that each blow advances the anvil (36) downward can be monitored and recorded. One non-limiting example of an option for monitoring this distance is to compare the zero position of the hammer (32) before a blow with the position of the hammer (32) following a blow.

Drop Height—Feedback

In the first exemplary embodiment, the drop height of the hammer (32) is controlled in part by reducing the hammer lifting speed between the ramp-down position of the hammer (32) and the maximum lifting height.

In the first exemplary embodiment, the reduction of the hammer lifting speed between the ramp-down position of the hammer (32) and the maximum lifting height is based upon a fixed ramp-down model which does not utilize feedback from the system (20). The fixed ramp-down model requires all of the system (20) parameters to be consistent in order to work successfully.

In other embodiments, the reduction of the hammer lifting speed could be adjusted based on feedback relating to one or more system (20) parameters. As a non-limiting example, the difference between the required drop height and the actual drop height for a previous drop of the hammer (32) may be used to adjust the ramp-down parameters for a subsequent lifting of the hammer (32).

Alternatively, the drop height of the hammer (32) may be controlled in part by the zero position of the hammer (32). As a non-limiting example, the difference between the required drop height and the actual drop height for a previous drop of the hammer (32) may be used to adjust the zero position of the hammer (32) within the hammer assembly (30) for a subsequent lifting of the hammer (32).

Split Spoon Bounce

If the soil in which the standard penetration test is being performed is extremely hard, a phenomenon described as "split spoon bounce" may occur during the standard penetration test, in which the split spoon sampler (not shown) at the distal end of the sampler string bounces in response to a blow from the hammer (32). If large enough, this split spoon bounce may cause the system to "false pause" the test.

In the first exemplary embodiment, the system (20) is configured to detect split spoon bounce and to override such false pauses through the use of the anvil sensor (84) to sense oscillating movement of the anvil (36) due to split spoon bounce.

The Second Exemplary Embodiment

The second exemplary embodiment of the system (20) for performing a standard penetration test is similar to the first exemplary embodiment, but omits the 3 proximity sensors (84, 86, 82). As a result, the second exemplary embodiment includes only 2 linear displacement sensors (50, 52). The second exemplary embodiment of the system (20) may be used to perform a second exemplary embodiment of a method for performing a standard penetration test.

The hammer sensor (50), comprising a first linear displacement sensor, tracks the hammer (32) within the hammer assembly (30) and the elevator sensor (52), comprising a second linear displacement sensor, tracks the elevator piston (76) within the elevator cylinder (74). A linear transducer that is capable of tracking at a suitable resolution an object moving at velocities up to those which may be experienced by the hammer (32) as it is dropped is used in the second exemplary embodiment as the hammer sensor (50) so that the energy of the dropped hammer (32) at impact with the anvil (36) can be determined.

An objective of the second exemplary embodiment of the system (20) is to deliver all the functionality of the first exemplary embodiment with the added benefits of velocity/energy detection and the ability to retro-fit conventional standard penetration test systems with minimal changes.

Referring to FIGS. 5-9, the second exemplary embodiment of the system (20) may be operated as follows to provide a second exemplary embodiment of a method for performing a standard penetration test:

1. in preparation for a standard penetration test, the hammer (32) is at rest at its bottom position within the hammer housing (60). In some configurations of the second exemplary embodiment, the hammer sensor (50) may sense whether the hammer (32) is at its bottom position, and if the hammer (32) is not at the bottom position, the system (20) will notify the operator and will not allow a test to begin. When the hammer (32) is first installed within the hammer housing (60), the system (20) uses a "set bottom position" function to sense and record the bottom position of the hammer (32) within the hammer assembly (30). Although the bottom position of the hammer (32) is stored by the system (20) and should never change for that hammer (32), the system (20) (via an administration screen) allows the bottom position to be reset if necessary;

2. the anvil (30) (which may have but does not require a recess (120)) is inserted within the hammer housing (60) with the hammer (32) resting on it. In the second exemplary embodiment, the system tracks the position of the hammer (32) as the anvil (36) pushes up on it. In order for a test to start or continue, the hammer (32) must be positioned above its bottom position. This feature prevents an inadvertent start-up of the system if the anvil (36) is not received within the hammer assembly (30). Initially, by default the zero position of the hammer (32) is considered to be 6.0 inches above the bottom position of the hammer (32). This distance is currently based upon the physical dimensions of the hammer assembly (30) and is subject to further optimization. Once the test begins, the zero position of the hammer (32) will become dynamic and will adjust up and down based upon what the actual drop heights of the hammer (32) in previous drops of the hammer (32). In order for the test to begin, the hammer (32) must be between the bottom position of the hammer (32) and the default zero position of the hammer (32). This allows the system to control the starting position of the hammer (32) by lowering the hammer (32) into position with the elevator assembly (40). The hammer assembly (30) is considered to be in the hammer assembly ready position if the hammer (32) is positioned between the bottom position and the default zero position;

3. in the second exemplary embodiment, if the hammer sensor (50) senses that the hammer (32) is positioned within the hammer housing (60) above its bottom position (thereby indicating that the anvil (36) is received within the hammer assembly (30)), the operator will be able to push a start button in order to lower the hammer assembly (30) with the elevator assembly (40) until the hammer (32) is positioned at its default zero position (6.0 inches above the bottom position). At this point, a stop command is sent to the elevator assembly (40) and the position sensed by the elevator sensor (52) is recorded as an initial reference position of the hammer assembly (30) relative to the elevator assembly (40). With hydraulic systems, there is always a little bit of overflow. Because of this overflow, a time delay of 300 ms is added to allow the system to settle and to allow an accurate hammer position to be recorded with the hammer sensor. This hammer position is the zero position of the hammer (32);

4. the chain drive motor is commanded to start rotating the chain drive, which causes the lift link (62) to engage and lift the hammer (32). In the second exemplary embodiment, the chain drive motor is initially driven at 70 percent of its maximum speed to provide an initial hammer lifting speed. The position of the hammer (32) within the hammer assembly (30) is tracked by the hammer sensor (50) as the hammer (32) is lifted. In the second exemplary embodiment, when the hammer (32) is lifted to 24.4 inches above the zero position, the speed of the chain drive motor and the hammer lifting speed begin to reduce;

5. in the second exemplary embodiment, the position of the hammer (32) within the hammer assembly (30) controls the ramp-down of the hammer lifting speed at a rate of 20% per inch to a minimum chain drive speed of 20 percent of the maximum speed of the chain drive motor. It is important that the valve of the hydraulic system which drives the chain drive motor produces a consistent flow for the ramp-down of the hammer lifting speed to be reliable. Because of the reliance on hydraulic flow, in the second exemplary embodiment the RPM of the rig engine (not shown) is automatically set to a minimum of 50% of the maximum allowed RPM when the standard penetration test begins. In other embodiments, other steps may be taken to ensure that an adequate and consistent flow of hydraulic fluid is provided to components of the system (20) such as the chain drive motor;

6. in the second exemplary embodiment, the ramp-down of the hammer lifting speed reduces the inertia of the hammer (32) so that when the lift link (62) disengages from the hammer (32) at the maximum lifting height, the hammer (32) is "tossed" upward about 0.75 inch to the drop position of the hammer (32). In the second exemplary embodiment, the hammer sensor (50) senses the drop position before the hammer (32) drops, and senses a reversal in direction of the hammer (32) from the drop position and counts the occurrence as a lift event. The difference between the drop position and the zero position represents the actual drop height and is recorded as the actual drop height for the drop of the hammer (32) upon the anvil (36). The actual drop height is compared with the ASTM standard (D1586-11) range of 29-31 inches. If the actual drop height falls within the standard range the drop is recorded as a passed drop. If the actual drop height falls outside the standard range the drop is recorded as a failed drop;

7. in the second exemplary embodiment, after the drop of the hammer (32) is sensed by the hammer sensor (50), the final reduced ramp-down speed of the chain drive motor is continued for 600 ms which provides time for the hammer (32) to impact the anvil (36), for the hammer sensor (50) to sense whether the anvil (36) remains in its desired location relative to the hammer assembly (30) and if necessary, for the elevator assembly (40) to reposition the hammer assembly (30) at the hammer assembly ready position. If the hammer assembly ready position has not been established by the end of the 600 ms, the chain drive motor is commanded to stop. If the hammer assembly ready position has been established by the end of the 600 ms, the chain drive motor resumes travel at full speed (i.e., at 70 percent of its maximum speed);

8. in the second exemplary embodiment, as the hammer (32) falls, the hammer sensor (50) is tracking its velocity every 5 ms. The kinetic energy of the hammer (32) at the point of impact with the anvil (36) can be determined from the velocity of the hammer (32) immediately prior to impact. Theoretically, the hammer (32) can reach a maximum velocity of 152 in/s (3.87 m/s) at impact for a 30 inch drop of the hammer (32). In the second exemplary embodiment, the resolution of the hammer sensor (50) is 5 ms (but is subject to further optimization), so the velocity of the hammer (32) at impact with the anvil (36) has the potential to be out by 11.8 J or 2.5%. Since the ASTM required drop height is a range of between 29-31 inches, which provides a theoretical energy difference of 31.65 J, a hammer sensor (50) with resolution of 5 ms will be suitable for use as a velocity/energy sensor. The velocity/energy of the hammer (32) immediately prior to impact with the anvil (36) is recorded for each blow of the hammer (32);

9. in the second exemplary embodiment, when the hammer (32) impacts the anvil (36), the anvil (36) is advanced downward. The hammer sensor (50) will sense that the new position of the hammer (32) within the hammer assembly (30) is below the zero position. The difference between the current position of the hammer (32) and the zero position of the hammer (32) is recorded as the distance of advancement of the anvil (36) for that blow of the hammer (32) (and is important information along with the velocity/energy of the hammer (32)). As a result of the new position of the hammer (32) being below the zero position, a command is sent to the elevator assembly (40) to reposition the hammer assembly (30) at the hammer assembly ready position. The hammer assembly (30) continues to be lowered by the elevator assembly (40) until the hammer sensor (50) senses that the hammer (32) has returned to its zero position, at which point a stop command is issued to the elevator assembly (40). The time delay of 300 ms is provided again to account for hydraulic overflow. The position of the hammer (32) within the hammer assembly (30) is sensed by the hammer sensor (50) and recorded as an updated zero position of the hammer (32). The zero position of the hammer (32) is now dynamic, and the updated zero position is adjusted based upon feedback from the system (20). If the actual drop height for the previous drop of the hammer (32) is greater than 30 inches, the zero position of the hammer (32) will be raised by a percentage of that difference. If the actual drop height for the previous drop of the hammer (32) is less than 30 inches, the zero position will be lowered by a percentage of that difference. The percentage of the difference and other parameters for adjusting the zero position of the hammer (32) are subject to further optimization;

10. in the second exemplary embodiment, the above described procedure is repeated until the elevator sensor (52) senses that the hammer assembly (30) has been lowered 18 inches relative to the initial reference position. The blows of the hammer (32) upon the anvil (36) are recorded in distance increments of 6 inches, so while the position of the hammer assembly (30) relative to the elevator assembly (40) is between 0-5.9 inches from the initial reference position the blows are counted towards a "first count", while the position of the hammer assembly (30) relative to the elevator assembly (40) is between 6-11.9 inches from the initial reference position the blows are counted towards a "second count", and while the position of the hammer assembly (30) relative to the elevator assembly (40) is between 6-17.9 inches from the initial reference position the blows are counted towards a "third count"; and 11. when the position of the hammer assembly (30) relative to the elevator assembly (40) has moved 18 inches from the initial reference position, the standard penetration test is stopped. Referring to FIG. 9, in the second exemplary embodiment the recorded data may be stored on a suitable storage medium (100) such as a disk and/or a server, and if desired may be made available via a computer network (106) to be accessed from a remote location (108).

The second exemplary embodiment of the system (20) and method may include additional features.

Bottom Stroke Detection Zone

In the second exemplary embodiment, the bottom stroke detection zone is implemented in the same manner as in the first exemplary embodiment.

Missing Anvil (36)

In the second exemplary embodiment, the anvil sensor (80) is omitted and the position of the anvil (36) is determined using the hammer sensor (50), with reference to the position of the hammer (32) within the hammer assembly (30).

Consequently, when the hammer (32) is installed in the hammer assembly (30), the bottom position of the hammer (32) within the hammer assembly (30) is sensed by the hammer sensor (50) and recorded by the system (20) so that the system (20) will be able to determine when the hammer (32) is resting within the hammer housing (60). As a result, an anvil (36) can be assumed to be missing during a test if the hammer (32) ever reaches the bottom position. To ensure that the bottom position is detected before the hammer (32) is supported in the hammer housing (60), a distance of 0.2 inch is added to the bottom position for the purpose of sensing a missing anvil (36).

In the second exemplary embodiment, when the anvil (36) is determined to be missing during a test, the test pauses as it does when the bottom stroke detection zone is encountered, but the system (20) continues to track the total test distance as the operator attempts to reposition the hammer assembly (30) at the hammer assembly ready position in order to continue the test. If the total test distance reaches 18 inches as the operator attempts to reposition the hammer assembly (30) at the hammer assembly ready position, the test is considered to be complete.

Right of Refusal Conditions

In the second exemplary embodiment, the right of refusal conditions are addressed in the same manner as in the first exemplary embodiment.

Soft Soil Detection

In the second exemplary embodiment, the soft soil detection issue is addressed in the same manner as in the first exemplary embodiment.

One Repositioning of the Hammer Assembly (30) Per Hammer Blow

In the second exemplary embodiment, the anvil sensor (80) is omitted and the position of the anvil (36) is determined using the hammer sensor (50), with reference to the position of the hammer (32) within the hammer assembly (30).

Consequently, once the zero position of the hammer (32) is established for a drop of the hammer (32) and the hammer (32) is lifted in preparation for a drop of the hammer (32), no command will be issued to the elevator assembly (40) to reposition the hammer assembly (30) until after the drop of the hammer (32) is completed. As a result, due to the omission of the anvil sensor (80), the possibility of a repositioning of the hammer assembly (30) after lifting of the hammer (32) has begun is eliminated in the second exemplary embodiment.

Aborted Tests

In the second exemplary embodiment, aborted tests are addressed in the same manner as in the first exemplary embodiment.

Split Spoon Bounce

In the second exemplary embodiment, if the hammer sensor (50) is sensitive enough and is capable of reacting quickly enough to detect the bounce, then split spoon bounce detection will be possible using the hammer sensor (50).

If the hammer sensor (50) cannot be used to detect split spoon bounce, split spoon bounce may be addressed in the same manner as in the first exemplary embodiment, using an anvil sensor (80) to sense the position of the anvil (36) independently of the hammer sensor (50).

The Third Exemplary Embodiment

A third exemplary embodiment of a method for performing a standard penetration test utilizes the same physical components as the second exemplary embodiment of the system (20), but eliminates the use of time delays in the system (20). Accordingly, the second exemplary embodiment of the system (20) may be adapted to perform the third exemplary embodiment of a method for performing a standard penetration test.

Hydraulic system behavior can vary dramatically from one drilling system to another. In the third exemplary embodiment, events have been established to control the order of functions of the system (20), regardless of the varying hydraulic system behaviors. In the third exemplary embodiment, nine events are used, based on the position of the hammer (32) within the hammer assembly (30). In other embodiments, fewer or greater than nine events may be used. In the third exemplary embodiment, an event uses ten proportional-integral-derivative (PID) control loops to control the motion of the hammer (32) in order to filter out any vibrations in the system (20). In other embodiments, fewer or greater than ten controller loops and/or other types of feedback control may be used. In the third exemplary embodiment, the events are defined as follows:

Event 1: the first event occurs when the hammer (32) is below zero position and is either not moving or moving up;

Event 2: the second event occurs when the hammer (32) comes within 0.5 inch of the zero position. A 1 inch "zero window" is established around the zero position to filter out overflow of the hydraulic system;

Event 3: the third event occurs when the hammer (32) settles within the zero window and is determined not to be moving;

Event 4: the fourth event occurs when the hammer (32) has moved above the zero window and is moving upward;

Event 5: the fifth event occurs when the hammer (32) is moving downward and is above the zero position;

Event 6: the sixth event occurs when the hammer (32) is moving downward and is below the zero position;

Event 7: the seventh event occurs when the hammer (32) bounces upon impact with the anvil (36) in hard soil conditions or for some other reason so that the system (20) can wait for the hammer (32) to settle before moving to the next event;

Event 8: the eighth event occurs when the third event transitions to the sixth event. This is an error event to flag when the hammer (32) has sunk in soft soil after it had previously been determined to have settled in the zero window; and Event 9: the ninth event occurs when the second event transitions to the fourth event. This is an error event to flag that the hammer (32) did not stop within the zero window.

An objective of the third exemplary embodiment is to deliver the functionality of the second exemplary embodiment with the added benefit of providing a more stable, repeatable system when installed on varying types of drilling equipment.

Referring to FIGS. 5-9, the second exemplary embodiment of the system (20) may be operated as follows to provide a third exemplary embodiment of a method for performing a standard penetration test:

1. in preparation for a standard penetration test, the hammer (32) is at rest at its bottom position within the hammer housing (60). In some configurations of the third exemplary embodiment, the hammer sensor (50) may sense whether the hammer (32) is at its bottom position, and if the hammer (32) is not at the bottom position, the system (20) will notify the operator and will not allow a test to begin. When the hammer (32) is first installed within the hammer housing (60), the system (20) uses a "set bottom position" function to sense and record the bottom position of the hammer (32) within the hammer assembly (30). Although the bottom position of the hammer (32) is stored by the system (20) and should never change for that hammer (32), the system (20) (via an administration screen) allows the bottom position to be reset if necessary;

2. the anvil (36) (which may have but does not require a recess (120)) is inserted within the hammer housing (60) with the hammer (32) resting on it. In the third exemplary embodiment, the system (20) tracks the position of the hammer (32) as the anvil (36) pushes up on it. In order for a test to start or continue, the hammer (32) must be positioned above its bottom position. This feature prevents an inadvertent start-up of the system (20) if the anvil (36) is not received within the hammer assembly (32). Initially, by default the zero position of the hammer (32) is considered to be 6.0 inches above the bottom position of the hammer (32). This distance is currently based upon the physical dimensions of the hammer assembly (30) and is subject to further optimization. In order for the test to begin, the hammer (32) must be between the bottom position of the hammer (32) and the default zero position of the hammer (32). This allows the system (20) to control the starting position of the hammer (32) by lowering the hammer (32) into position with the elevator assembly (40). The hammer assembly (30) is considered to be in the hammer assembly ready position if the hammer (32) is positioned between the bottom position and the default zero position;

3. in the third exemplary embodiment, if the hammer sensor (50) senses that the hammer (32) is positioned within the hammer housing (60) above its bottom position (thereby indicating that the anvil (36) is received within the hammer assembly (30)), the operator will be able to push a start button to begin the test. The system (20) is at Event 1, which sends a command to the elevator assembly (40) to move the hammer assembly (30) downward in order to raise the hammer (32) toward the zero window. The system (20) uses the distance from the hammer (32) position to the default zero position to adjust the PID controls relating to the motion of the elevator assembly (40) (as the hammer (32) approaches the default zero position, the elevator assembly (40) slows down). When the hammer (32) enters the zero window, Event 2 occurs, sending a stop command to the elevator assembly (40);

4. in the third exemplary embodiment, the hammer (32) settles to a position within the zero window causing Event 3 to occur. The position sensed by the elevator sensor (52) is recorded as an initial reference position of the hammer assembly (30) relative to the elevator assembly (40). This hammer (32) position is the zero position of the hammer (32). The PID control relating to lifting of the hammer (32) takes the difference of the zero position from the default zero position into account in a hammer velocity control algorithm. The chain drive motor is commanded to start rotating the chain drive, which causes the lift link (62) to engage and lift the hammer (32);

5. in the third exemplary embodiment, the hammer (32) causes Event 4 to occur when the hammer (32) moves above the zero window. The chain drive motor is driven at its maximum speed to provide an initial hammer lifting speed. The position of the hammer (32) within the hammer assembly (30) is tracked by the hammer sensor (50) as the hammer (32) is lifted. In the third exemplary embodiment, the speed of the chain drive motor and the hammer lifting speed begin to reduce with PID control. It is important that the valve of the hydraulic system which drives the chain drive motor produces a consistent flow for the PID control of the hammer lifting speed to be reliable. Because of the reliance on hydraulic flow, in the third exemplary embodiment the RPM of the rig engine (not shown) is monitored. If possible the RPM is automatically controlled, and if not, a warning is used to force operators to set the engine RPM to a desired rate which is determined during installation of the system (20). In other embodiments, other steps may be taken to ensure that an adequate and consistent flow of hydraulic fluid is provided to components of the system (20) such as the chain drive motor;

6. in the third exemplary embodiment, the PID control of the lifting of the hammer (32) reduces the inertia of the hammer (32) so that when the lift link (62) disengages from the hammer (32) at the maximum lifting height, the hammer (32) is "tossed" upward about 0.75 inch to the drop position of the hammer (32). The hammer sensor (50) senses the drop position before the hammer (32) drops, and senses a reversal in direction of the hammer (32) from the drop position and counts the occurrence as a lift event. The difference between the drop position and the zero position represents the actual drop height and is recorded as the actual drop height for the drop of the hammer (32) upon the anvil (36). The actual drop height is compared with the ASTM standard (D1586-11) range of 29-31 inches. If the actual drop height falls within the standard range the drop is recorded as a passed drop. If the actual drop height falls outside the standard range the drop is recorded as a failed drop;

7. in the third exemplary embodiment, the movement of the hammer (32) downward from the drop height causes Event 5 to occur. The chain drive motor is turned back to its maximum speed while the hammer (32) falls;

8. in the third exemplary embodiment, as the hammer (32) falls, the hammer sensor (50) is tracking the hammer velocity every 5 ms. The kinetic energy of the hammer (32) at the point of impact with the anvil (36) can be determined from the velocity of the hammer (32) immediately prior to impact. Theoretically, the hammer (32) can reach a maximum velocity of 152 in/s (3.87 m/s) at impact for a 30 inch drop of the hammer (32). In the third exemplary embodiment, the resolution of the hammer sensor (50) is 5 ms (but is subject to further optimization), so the velocity of the hammer (32) at impact with the anvil (36) has the potential to be out by 11.8 J or 2.5%. Since the ASTM required drop height is a range of between 29-31 inches, which provides a theoretical energy difference of 31.65 J, a hammer sensor (50) with resolution of 5 ms will be suitable for use as a velocity/energy sensor. The velocity/energy of the hammer (32) immediately prior to impact with the anvil (36) is recorded for each blow of the hammer (32);

9. in the third exemplary embodiment, when the hammer (32) impacts the anvil (36) the hammer (32) position is sensed by the hammer sensor (50) to determine the advancement of the anvil (36). Event 6 occurs when the hammer (32) moves downward below the zero position. When the hammer (32) is sensed to have stopped moving, Event 1 occurs again, and the advancement of the anvil (36) is determined by the difference between the current hammer (32) position and the hammer (32) zero position at the start of the lift. This advancement of the anvil (36) is used in the PID control of both the chain drive motor and the elevator assembly (40) to allow the elevator assembly (40) to reposition the hammer assembly (30) back to the hammer (32) zero position before the lift link (62) comes back around to pick up the hammer (32) for the next lift. If the advancement of the anvil (36) is very small, the chain drive motor will not slow down, but if the advancement of the anvil (36) is very large, the chain drive motor will slow down significantly;

10. in the third exemplary embodiment, if the hammer (32) bounces on impact because of hard soil conditions or for some other reason, Event 7 occurs telling the system (20) to look for Event 3 to occur again without first moving through Events 6, 1, and 2. If the hammer (32) settles below the zero window, Event 1 will occur and the procedure starts over as normal. If Event 4 occurs, which means the hammer (32) was unable to settle to find a new zero position before it was picked up by the lifting link (62) for the next drop, the chain drive is commanded to stop and the elevator assembly (40) repositions the hammer (32) back to the zero position, and the procedure starts over as normal. If Event 3 occurs, which means the advancement of the anvil (36) was too small to cause the elevator assembly (40) to reposition the hammer (32), a new zero position is recorded at the settle position of the hammer (32). This new zero position is closely monitored because the test depth is based on the position of the elevator assembly (40), and if the elevator assembly (40) does not move the test depth will not update. In this case, the advancement of the anvil (36) is used to update the test depth to determine if the next drop is supposed to be counted in the next count bin or remain in the previous count bin;

11. in the third exemplary embodiment, when the system (20) transitions normally from Event 6 to 1, the elevator assembly (40) repositions the hammer assembly (30) to move the hammer (32) position back to the zero position. When the hammer (32) position enters the zero window, Event 2 occurs again commanding the elevator assembly (40) to stop. When the hammer (32) position settles within the zero window, Event 3 occurs again, recording the hammer (32) position as the new zero position and updating the test depth by the change in position of the elevator assembly (40);

12. in the third exemplary embodiment, the system (20) can be paused by tripping a hammer assembly control joystick or by pressing the "pause" button on the display. To maintain the integrity of the test data, the system (20) will continue operation until it reaches a safe place to pause, such as but not necessarily limited to after the hammer (32) has dropped. The system (20) will not pause while the hammer (32) is being lifted as it will fall on the anvil (36) and compromise the test data. If an emergency occurs, the system (20) is connected into the drilling equipment electronic system (not shown) and the emergency stop button (not shown) for the drilling equipment (not shown) will also stop the system (20) abruptly, which may also result in compromised test data;

13. in the third exemplary embodiment, if Event 9 occurs the elevator assembly (40) will reposition the hammer assembly (30) to the zero position of the hammer (32). This error event safeguards against the elevator assembly (40) continuing to push down against the anvil (36) as a result of a mechanical failure in the system (20);

14. in the third exemplary embodiment, the above described procedure is repeated until the elevator sensor (52) senses that the hammer assembly (30) has been lowered 18 inches relative to the initial reference position. The PID controls use feedback from the drop heights recorded and the positions of the updated zero positions to adjust and maintain a consistent 30 inch drop to meet ASTM standards as well as to maximize test speed. In the third exemplary embodiment, the blows of the hammer (32) upon the anvil (36) are recorded in distance increments of 1 inch, so while the position of the hammer assembly (30) relative to the elevator assembly (40) is between 0-0.9 inches from the initial reference position the blows are counted towards a "count 1," while the position of the hammer assembly (30) relative to the elevator assembly (40) is between 1-1.9 inches from the initial reference position the blows are counted towards a "count 2," and so on until when the position of the hammer assembly (30) relative to the elevator assembly (40) is between 17-17.9 inches from the initial reference position the blows are counted towards a "count 18." In other embodiments, smaller or larger increments may be used. The ASTM standard requires blow counts to be separated into increments of 6 inches, so 1-6 inches are recorded as "first count," 7-12 inches are recorded as "second count," and 13-18 inches are recorded as "third count;" and 15. when the position of the hammer assembly (30) relative to the elevator assembly (40) has moved 18 inches from the initial reference position, the standard penetration test is stopped. Referring to FIG. 9, in the third exemplary embodiment the recorded data may be stored on a suitable storage medium (100) such as a disk and/or a server, and if desired may be made available via a computer network (106) to be accessed from a remote location (108).

The third exemplary embodiment of the system (20) and method may include additional features.

Bottom Stroke Detection Zone

In the third exemplary embodiment, the bottom stroke of the elevator assembly (40) is determined during system (20) installation. With the elevator assembly (40) lowered all the way downward, the position sensed by the elevator sensor (52) is stored by the system (20) during installation. 0.2 inches is added to the bottom stroke position to ensure detection. This allows for more efficient design of the system (20) for manufactured parts and configuring with varying drilling equipment systems. During a standard penetration test, if the bottom stroke detection zone is detected and the operator decides to add a rod extension (not shown) to continue, the test depth tracking takes the 0.2 inches into account when continuing the test.

In the third exemplary embodiment, when the bottom stroke detection zone is detected, the system (20) quickly checks to see if the advancement of the anvil resulting from the last blow would make the test complete. If so, the test is determined to be completed without having to add a rod extension to find out the same information. If the test is still not complete, then the operator is given the option by the system (20) to add a rod extension or abort the test at the displayed test depth.

Missing Anvil (36)

In the third exemplary embodiment, the missing anvil conditions are addressed in the same manner as in the second exemplary embodiment, but with the addition of a procedure to address the circumstance of the bottom stroke detection zone being detected in the process of correcting the missing anvil (36). If the anvil (36) is determined still to be missing when the operator is moving the hammer assembly (30) back over the anvil (36) in order to continue the test and encounters the bottom stroke detection zone, the test pauses with no option to continue. In this condition the system (20) cannot continue because it has lost the correlation between the position of the hammer (32) and the position of the elevator assembly (40). The system (20) allows the operator to abort the test at the displayed test depth, or to override the test to set it as complete with the acknowledgment that the operator has made the decision based on parameters outside the system (20), such as but not limited to chalk marks on the rods.

Right of Refusal Conditions

In the third exemplary embodiment, the right of refusal conditions are addressed in the same manner as in the first exemplary embodiment.

Soft Soil Detection

In the third exemplary embodiment, the soft soil detection issue is addressed in the same manner as in the first exemplary embodiment, except that all time delays are replaced with events, and with the addition of providing a procedure for starting the test in soft soils. The system will allow the operator to confirm that the hammer (32) is in contact with the anvil (36) and will allow the standard penetration test to start without having to position the hammer assembly (32) into the hammer assembly ready position. This procedure allows standard penetration tests to be performed in very soft soils without losing the integrity of the test. Any sinking of the anvil (36) is addressed as previously described, with the modified conditions of the third exemplary embodiment for bottom stroke detection and missing anvil (36) conditions.

In the third exemplary embodiment, Event 8 tracks when the anvil (36) sinks after the zero position of the hammer (32) is set but before the lift link (62) can pick up the hammer (32). If the anvil (36) sinks the drop height for the drop would be inaccurate and the lift link (62) may run into the side of the hammer (32) binding it in the hammer assembly (30). This error event allows the elevator assembly (40) to reposition the hammer assembly (30) back to the zero position of the hammer (32) without compromising the integrity of the test data.

One Repositioning of the Hammer Assembly (30) Per Hammer (32) Blow

In the third exemplary embodiment, the limit of one repositioning of the hammer assembly (30) per hammer (32) blow is addressed in the same manner as in the second exemplary embodiment.

Aborted Tests

In the third exemplary embodiment, aborted tests are addressed in the same manner as in the first exemplary embodiment.

Split Spoon Bounce

In the third exemplary embodiment, the hammer sensor (50) can detect both the hammer (32) bouncing and the advancement of the anvil (36). Using these parameters, a determination of spilt spoon bounce can be interpreted.

In this document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

We claim:

1. A system for performing a standard penetration test comprising:
   (a) a hammer assembly comprising a hammer housing, a hammer contained within the hammer housing, and a hammer lifting device for lifting the hammer;
   (b) an elevator assembly for raising and lowering the hammer assembly, wherein the elevator assembly comprises a mount and an elevator drive, wherein the mount is connected with the hammer assembly, and wherein the mount is reciprocable vertically along the elevator assembly by the elevator drive;
   (c) a hammer sensor associated with the hammer housing and the hammer, for sensing a position of the hammer within the hammer housing relative to a bottom position of the hammer within the hammer housing; and
   (d) an elevator sensor associated with the elevator drive for sensing an initial reference position and a plurality of updated reference positions of the hammer assembly relative to the elevator assembly, wherein the standard penetration test is complete when the elevator sensor senses that the hammer assembly has been lowered during the standard penetration test a standard test distance relative to the initial reference position.

2. The system as claimed in claim 1 wherein the elevator drive comprises an elevator cylinder and an elevator piston reciprocably contained within the elevator cylinder.

3. The system as claimed in claim 2 wherein the elevator sensor is associated with the elevator cylinder and the elevator piston so that sensing the position of the hammer assembly relative to the elevator assembly comprises sensing a position of the elevator piston relative to the elevator cylinder.

4. The system as claimed in claim 3 wherein the elevator sensor comprises a linear displacement sensor.

5. The system as claimed in claim 1 wherein the hammer lifting device engages with the hammer to lift the hammer and disengages from the hammer to allow the hammer to drop.

6. The system as claimed in claim 5 wherein the hammer lifting device comprises a chain drive and wherein the chain drive comprises a lift link for engaging with the hammer in order to lift the hammer.

7. The system as claimed in claim 1 wherein the hammer sensor comprises a linear displacement sensor.

8. The system as claimed in claim 1 wherein the hammer assembly comprises a lift counter, wherein the lifting of the hammer is a lift event, and wherein the lift counter counts lift events.

9. The system as claimed in claim 8 wherein the lift counter comprises a proximity sensor.

10. The system as claimed in claim 9 wherein the hammer lifting device comprises a chain drive, wherein the chain drive comprises a lift link for engaging with the hammer in order to lift the hammer, and wherein the lift counter senses the lift link in order to count lift events.

11. The system as claimed in claim 1 wherein the hammer assembly is configured to drop the hammer onto an anvil and wherein the hammer assembly comprises an anvil position sensor for sensing a position of the anvil relative to the hammer assembly.

12. The system as claimed in claim 11 wherein the anvil position sensor comprises one or more proximity sensors.

13. The system as claimed in claim 12 wherein the anvil position sensor comprises a first proximity sensor for providing an indication of whether the anvil is positioned at a desired location relative to the hammer assembly.

14. The system as claimed in claim 13 wherein the anvil defines a recess and wherein the anvil is positioned at the desired location relative to the hammer assembly when the first proximity sensor senses the recess.

15. The system as claimed in claim 13 wherein the anvil position sensor comprises a second proximity sensor for providing an indication of whether the anvil is received within the hammer housing.

16. The system as claimed in claim 15 wherein the anvil is received within the hammer housing when the second proximity sensor senses the anvil.

17. The system as claimed in claim 1 wherein the hammer assembly is configured to drop the hammer onto an anvil and wherein the hammer assembly comprises a velocity sensor for sensing an anvil contact velocity of the hammer as the hammer contacts the anvil.

18. The system as claimed in claim 1 wherein the hammer assembly is configured to drop the hammer onto an anvil and wherein the hammer assembly comprises an energy sensor for sensing an anvil contact energy which is delivered from the hammer to the anvil as the hammer contacts the anvil.

19. The system as claimed in claim 1, further comprising a storage medium for storing data related to the standard penetration test.

20. The system as claimed in claim 19, further comprising a computer network connected with the storage medium, for enabling remote access to the stored data.

21. A method for performing a standard penetration test comprising:
   (a) providing:
      a hammer assembly comprising a hammer housing, a hammer contained within the hammer housing, and a hammer lifting device for lifting the hammer;
      (ii) an elevator assembly for raising and lowering the hammer assembly, wherein the elevator assembly comprises a mount and an elevator drive, wherein the mount is connected with the hammer assembly, and wherein the mount is reciprocable vertically along the elevator assembly by the elevator drive;
      (iii) a hammer sensor associated with the hammer housing and the hammer, for sensing a position of the hammer within the hammer housing relative to a bottom position of the hammer within the hammer housing; and
      (iv) an elevator sensor associated with the elevator drive for sensing an initial reference position and a plurality of updated reference positions of the hammer assembly relative to the elevator assembly, wherein the standard penetration test is complete when the elevator sensor senses that the hammer assembly has been lowered during the standard penetration test a standard test distance relative to the initial reference position;

(b) positioning the hammer assembly at a hammer assembly ready position wherein an anvil is positioned at a desired location relative to the hammer assembly and wherein the hammer is resting upon the anvil;

(c) sensing with the elevator sensor the initial reference position of the hammer assembly relative to the elevator assembly when the hammer assembly is positioned at the hammer assembly ready position;

(d) sensing with the hammer sensor a zero position of the hammer within the hammer housing when the hammer assembly is positioned at the hammer assembly ready position, wherein the bottom position of the hammer is below the zero position of the hammer;

(e) lifting the hammer with the hammer lifting device from the zero position of the hammer to a drop position of the hammer within the hammer housing;

sensing with the hammer sensor the drop position of the hammer within the hammer housing; and (g) dropping the hammer onto the anvil from the drop position.

22. The method as claimed in claim 21, further comprising determining an actual drop height of the hammer from the drop position of the hammer and the zero position of the hammer.

23. The method as claimed in claim 22, further comprising comparing the actual drop height of the hammer with a required drop height for the standard penetration test, and further comprising identifying the actual drop height as either compliant or non-compliant with the required drop height.

24. The method as claimed in claim 21 wherein lifting the hammer from the zero position of the hammer to the drop position of the hammer comprises engaging the hammer lifting device with the hammer at the zero position, disengaging the hammer lifting device from the hammer at a maximum lifting height, and allowing inertia to lift the hammer from the maximum lifting height to the drop position.

25. The method as claimed in claim 24 wherein the hammer is lifted by the hammer lifting device at a hammer lifting speed and wherein lifting the hammer from the zero position of the hammer to the drop position of the hammer comprises reducing the hammer lifting speed before the hammer reaches the maximum lifting height in order to reduce the inertia of the hammer.

26. The method as claimed in claim 25 wherein the hammer lifting speed is reduced incrementally between a ramp-down position of the hammer within the hammer assembly and the maximum lifting height.

27. The method as claimed in claim 21, further comprising determining if the anvil is positioned at the desired location relative to the hammer assembly.

28. The method as claimed in claim 27 wherein determining if the anvil is positioned at the desired location relative to the hammer assembly comprises sensing with an anvil position sensor a position of the anvil relative to the hammer assembly.

29. The method as claimed in claim 28 wherein the anvil defines a recess and wherein the anvil is positioned at the desired location relative to the hammer assembly when the anvil position sensor senses the recess.

30. The method as claimed in claim 28 wherein the anvil is received within the hammer housing when the anvil position sensor senses the anvil.

31. The method as claimed in claim 21, further comprising counting the lifting of the hammer as a lift event.

32. The method as claimed in claim 31 wherein counting the lifting of the hammer comprises sensing a position of the hammer within the hammer assembly.

33. The method as claimed in claim 31 wherein counting the lifting of the hammer comprises sensing a position of the hammer lifting device.

34. The method as claimed in claim 20 wherein the hammer contacts the anvil at an anvil contact velocity after it is dropped, further comprising sensing the anvil contact velocity.

35. The method as claimed in claim 20 wherein the hammer delivers an anvil contact energy to the anvil after it is dropped, further comprising sensing the anvil contact energy.

36. The method as claimed in claim 20, further comprising:

(h) repositioning the hammer assembly at the hammer assembly ready position after dropping the hammer onto the anvil;

sensing with the elevator sensor an updated reference position of the hammer assembly relative to the elevator assembly when the hammer assembly is repositioned at the hammer assembly ready position;

sensing with the hammer sensor an updated zero position of the hammer within the hammer housing when the hammer assembly is repositioned at the hammer assembly ready position;

(k) lifting the hammer with the hammer lifting device from the updated zero position of the hammer to the drop position of the hammer within the hammer housing;

(l) sensing with the hammer sensor the drop position of the hammer within the hammer housing;

(m) dropping the hammer onto the anvil from the drop position; and (n) repeating (h) through (m) until the standard penetration test is complete.

37. The method as claimed in claim 36, further comprising storing data related to the standard penetration test on a storage medium.

38. The method as claimed in claim 37, further comprising accessing the stored data from a remote location.

39. The method as claimed in claim 23, further comprising:

(h) repositioning the hammer assembly at the hammer assembly ready position after dropping the hammer onto the anvil;

(i) sensing with the elevator sensor an updated reference position of the hammer assembly relative to the elevator assembly when the hammer assembly is repositioned at the hammer assembly ready position;

(j) sensing with the hammer sensor an updated zero position of the hammer within the hammer housing when the hammer assembly is repositioned at the hammer assembly ready position;

(k) lifting the hammer with the hammer lifting device at a hammer lifting speed from the updated zero position of the hammer to the drop position of the hammer within the hammer housing, wherein the hammer lifting speed is selected having regard to an actual drop height of a previous drop of the hammer;

(l) sensing with the hammer sensor the drop position of the hammer within the hammer housing; and (m) dropping the hammer onto the anvil from the drop position.

40. The method as claimed in claim 39 wherein lifting the hammer from the updated zero position of the hammer to the drop position of the hammer comprises engaging the hammer lifting device with the hammer at the updated zero position, disengaging the hammer lifting device from the hammer at a maximum lifting height, and allowing inertia to lift the hammer from the maximum lifting height to the drop position.

41. The method as claimed in claim 40 wherein lifting the hammer from the updated zero position of the hammer to the drop position of the hammer comprises reducing the hammer lifting speed before the hammer reaches the maximum lifting height in order to reduce the inertia of the hammer.

42. The method as claimed in claim 41 wherein the hammer lifting speed is reduced incrementally between a ramp-down position of the hammer within the hammer assembly and the maximum lifting height.

43. The system as claimed in claim 19, further comprising a global positioning system receiver for providing geographical data relating to a geographical location of the standard penetration test, and wherein the stored data comprises the geographical data.

44. The method as claimed in claim 37, further comprising collecting geographical data relating to a geographical location of the standard penetration test, and wherein the stored data comprises the geographical data.

* * * * *